United States Patent
Yu et al.

(10) Patent No.: US 12,299,877 B2
(45) Date of Patent: May 13, 2025

(54) MEDICAL IMAGE ANALYSIS APPARATUS AND METHOD, AND MEDICAL IMAGE VISUALIZATION APPARATUS AND METHOD

(71) Applicant: CORELINE SOFT CO., LTD., Seoul (KR)

(72) Inventors: Donghoon Yu, Gimpo-si (KR); Jaeyoun Yi, Seoul (KR)

(73) Assignee: CORELINE SOFT CO, LTD., Seoul (KR)

(*) Notice: Subject to any disclaimer, the term of this patent is extended or adjusted under 35 U.S.C. 154(b) by 339 days.

(21) Appl. No.: 17/746,347

(22) Filed: May 17, 2022

(65) Prior Publication Data

US 2022/0366562 A1    Nov. 17, 2022

(30) Foreign Application Priority Data

May 17, 2021    (KR) .................. 10-2021-0063580

(51) Int. Cl.
   *G06T 7/00*      (2017.01)
   *G16H 30/20*    (2018.01)
   *G16H 30/40*    (2018.01)

(52) U.S. Cl.
   CPC .......... *G06T 7/0012* (2013.01); *G16H 30/20* (2018.01); *G16H 30/40* (2018.01); *G06T 2207/30061* (2013.01)

(58) Field of Classification Search
   CPC ......... G06T 7/0012; G06T 2207/30061; G06T 2211/416; G16H 30/20; G16H 30/40;
   (Continued)

(56) References Cited

U.S. PATENT DOCUMENTS 7,688,995 B2    3/2010   Stoeckel
8,165,368 B2    4/2012   VijayKalyan et al.
(Continued)

FOREIGN PATENT DOCUMENTS

JP    2008-188214 A    8/2008
JP    5782852 B2       7/2015
(Continued)

OTHER PUBLICATIONS

Machine translation for KR 10-1943011 (Year: 2019).*
(Continued)

*Primary Examiner* — Qian Yang
(74) *Attorney, Agent, or Firm* — United One Law Group LLC; Kongsik Kim; Jhongwoo Peck

(57) ABSTRACT

A medical image visualization apparatus includes a reception interface configured to receive at least one medical image; at least one processor; and a display. The at least one processor is configured to recognize a connection image that is presented on the at least one medical image and connects the at least one medical image and detailed analysis information regarding the at least one medical image; acquire the detailed analysis information, connected to the at least one medical image by the connection image; and visualize the detailed analysis information on the display. The detailed analysis information includes an intermediate result and a final result of a first process in which an image analysis result of an original medical image is generated as the at least one medical image.

12 Claims, 18 Drawing Sheets

(58) Field of Classification Search
CPC ........ G16H 80/00; G16H 15/00; G16H 40/60; G16H 50/20

See application file for complete search history.

(56) References Cited

U.S. PATENT DOCUMENTS

| | | | |
|---|---|---|---|
| 8,923,580 | B2 | 12/2014 | Dekel et al. |
| 9,773,305 | B2 | 9/2017 | Lee et al. |
| 10,445,462 | B2 | 10/2019 | Sorenson et al. |
| 10,945,807 | B2 | 3/2021 | Gibby et al. |
| 2007/0036412 | A1 | 2/2007 | Stoeckel |
| 2013/0163835 | A1 | 6/2013 | Park |
| 2014/0122515 | A1* | 5/2014 | Lee .................. G16Z 99/00 707/758 |
| 2014/0372149 | A1 | 12/2014 | Friese et al. |
| 2019/0356479 | A1 | 11/2019 | Grimme |
| 2019/0365498 | A1 | 12/2019 | Gibby et al. |
| 2019/0371454 | A1* | 12/2019 | Yu .................. G16H 30/40 |

FOREIGN PATENT DOCUMENTS

| | | |
|---|---|---|
| JP | 2017-182244 A | 10/2017 |
| KR | 10-1176448 B1 | 8/2012 |
| KR | 10-2014-0055152 A | 5/2014 |
| KR | 10-2014-0091176 A | 7/2014 |
| KR | 10-2014-0147999 A | 12/2014 |
| KR | 10-1611687 B1 | 4/2016 |
| KR | 10-1684998 B1 | 12/2016 |
| KR | 10-1818074 B1 | 1/2018 |
| KR | 10-1874348 B1 | 7/2018 |
| KR | 10-2018-0138107 A | 12/2018 |
| KR | 10-1938992 B1 | 1/2019 |
| KR | 10-1943011 * | 1/2019 |
| KR | 10-1943011 B1 | 1/2019 |
| KR | 10-2019-0105210 A | 9/2019 |
| KR | 10-2019-0117187 A | 10/2019 |
| KR | 10-2019-0138106 A | 12/2019 |
| KR | 10-2021-0013830 A | 2/2021 |
| KR | 10-2021-0014893 A | 2/2021 |

OTHER PUBLICATIONS

Lee et al., "Design and Implementation of Medical Information System Using QR Code," Journal of Internet Computing and Services, Apr. 2015, 16(2), 109-15.

* cited by examiner

MEDICAL IMAGE ANALYSIS APPARATUS AND METHOD, AND MEDICAL IMAGE VISUALIZATION APPARATUS AND METHOD

CROSS-REFERENCE TO RELATED APPLICATION

This application claims priority from Korean Patent Application No. 10-2021-0063580 filed on May 17, 2021, which is incorporated herein by reference in its entirety.

TECHNICAL FIELD

The present invention relates to an apparatus and method for assisting diagnosis using a medical image. More particularly, the present invention relates to a medical image analysis process and a visualization process of the analysis results.

BACKGROUND ART

There is an attempt to acquire additional information via a mobile terminal or wearable terminal by adding a QR code or barcode to a medical image.

As an example of the attempt, a system for providing medical information disclosed in Japanese Patent Application Publication No. 2017-182244 entitled "System for Providing Medical Information" searches for medical information related to information about the site of a patient based on the information about the site of the patient obtained via medical image acquisition equipment (modality) such as an ultrasound diagnostic apparatus, generates URL information for access to retrieved and selected medical information as a QR code, adds the QR code to a medical image including an image of the side of the patient, and outputs the medical image to which the QR code has been added.

Japanese Patent Application Publication No. 2017-182244 discloses a well-known QR code-combined medical image generation and storage means that is based on the concept of generating an access path to medical information related to an original medical image obtained via a modality as a QR code image and then storing a new medical image in data storage by combining the QR code image with the original medical image.

U.S. Patent Application Publication No. 2019/0356479 entitled "Method, Server and Communication System for Secure Delivery of Patient's Image and Consent Data" introduces a technology that allocates the recognition information of a patient in the form of a QR code when registering the patient and then uses the QR code as a medium for the authentication of a patient's UID and access to personal medical data.

U.S. Pat. No. 10,945,807 entitled "Augmented Reality Viewing and Tagging for Medical Procedures" introduces an interface that recognizes a QR code tag worn by a patient and then provides the patient's information to smart glasses worn by a doctor using an augmented reality technique.

These related art documents provide a variety of interfaces that provide a user with an electronic medical record (EMR) stored in a hospital system for a patient, an original medical image obtained for the patient, and the like via a QR code.

As another example, Korean Patent Application Publication No. 10-2019-0138106 entitled "Picture Archiving and Communication System" discloses the process of inserting a connection image, generated to connect an original medical image and analysis information, into a generated new medical image, the process of outputting the new medical image into which the connection image is inserted, and the process of visualizing the new medical image and the analysis information after recognizing the connection image.

In this case, the connection image connects the new medical image and the analysis information of the original medical image. However, the technology of Korean Patent Application Publication No. 10-2019-0138106 is implemented in a Picture Archiving and Communication System (PACS), and is problematic in that since analysis information is visualized as only an analysis image, a user can check only an analysis result generated as the analysis image but cannot obtain information about a process in which the analysis result is generated.

SUMMARY OF THE DISCLOSURE

An object of the present invention is to provide a user interface and display environment that increase the efficiency of the reading of a medical image performed by a radiologist and/or the efficiency of the diagnosis of a medical image performed by a clinician and assist a radiologist and/or a clinician in obtaining more accurate reading and/or diagnosis results within a short period of time, thereby increasing the accuracy of analysis.

An object of the present invention is to provide a user menu configured to, when a medical professional rejects artificial intelligence-based analysis and quantification results, allow a user to reject preprocessing results from which the analysis and quantification results are derived and also allow a user to re-perform a preprocessing process, an analysis process, and a quantification process in a manner independent of artificial intelligence.

It may be insufficient if an intermediate result is provided to the user only in the form of an image. A user may often determine whether an intermediate result is appropriate only when a menu configured to allow the user to interactively check each of the objects and/or values included in the intermediate result is additionally provided. Accordingly, an object of the present invention is to provide a user with a menu, through which the user can interactively check each of the objects and/or values of an intermediate result obtained during a processing process of computer software, via a connection image.

A user who is a medical professional may have a doubt about or may not be confident with an intermediate result or want to suggest an alternative after checking the intermediate result. The user may want to obtain a new intermediate result by changing the characteristic settings or threshold of the intermediate result and then obtain a new final result from the new intermediate result. An object of the present invention is to provide a work environment and user menu configured to allow the user to generate a new intermediate result by changing a characteristic setting or value required for the generation of an intermediate result so that the intermediate result obtained in the processing process of computer software can be newly obtained.

A user who is a medical professional may want to newly adjust a final result by using a new intermediate result. Alternatively, a user who is a medical professional may want to adjust only a final result while using an existing intermediate result without change. An object of the present invention is to provide a work environment and user menu configured to allow a user to generate a new final result by changing a characteristic setting or value required for the generation of a final result so that the final result obtained during a processing process of computer software based on an intermediate result can be newly obtained.

According to an embodiment of the present invention, there is provided a medical image visualization apparatus comprising a reception interface configured to receive at least one medical image; at least one processor; and a display. The at least one processor is further configured to recognize a connection image that is presented on the at least one medical image and connects the at least one medical image and detailed analysis information regarding the at least one medical image; acquire the detailed analysis information, connected to the at least one medical image by the connection image; and visualize the detailed analysis information on the display. The detailed analysis information includes an intermediate result and a final result of a first process in which an image analysis result of an original medical image is generated as the at least one medical image.

The detailed analysis information may include image information and non-image information regarding the intermediate result and the final result of the first process.

The at least one processor may be further configured to visualize the detailed analysis information together with a menu configured to allow a user to input feedback on the user's approval for or rejection of at least one of the intermediate result and the final result of the first process.

The at least one processor may be further configured to, when the user approves at least one of the intermediate result and the final result, store an indication of the user's approval of at least one of the intermediate result and the final result in association with the at least one medical image and the detailed analysis result in a database.

The at least one processor may be further configured to connect a work environment menu configured to allow a user to manually modify at least one of the intermediate result and the final result with the connection image; and provide the work environment menu together with the detailed analysis information.

The detailed analysis information may include a preprocessing result of the original medical image as the intermediate result; and a quantitative analysis result of the original medical image, generated based on the preprocessing result, as the final result.

The detailed analysis information may include an object identification result of the original medical image as the intermediate result; and a filtering result, obtained by applying a threshold to the object identification result, as the final result.

The at least one processor may be further configured to connect a menu configured to allow a user to edit the at least one medical image or to generate a new medical image in which settings of the at least one medical image are adjusted with the connection image; and provide the menu together with the detailed analysis information.

The at least one processor may be further configured to connect a work environment menu configured to, when the at least one medical image is at least one of an reconstructed image and a reformatted image of the original medical image, allow the user to generate at least one of a new reconstructed image and a new reformatted image as a new medical image by adjusting at least one of a range, an angle, a viewpoint, and an option in, at, from, and in which the at least one of the reconstructed image and the reformatted image is generated with the connection image; and provide the work environment menu together with the detailed analysis information.

The at least one processor may be further configured to connect a work environment menu configured to, when the at least one medical image includes a report indicative of the image analysis result, allow the user to generate a new report by adjusting at least one parameter used to generate the report with the connection image; and provide the work environment menu together with the detailed analysis information.

The at least one processor may be further configured to connect a work environment menu configured to, when the detailed analysis information includes an object identification result of the original medical image, allow the user to correct a threshold applied to the object identification result, to generate a result obtained by performing filtering while applying a modified threshold as new detailed analysis information, or to manually verify the object identification result before a threshold is applied with the connection image; and provide the work environment menu together with the detailed analysis information.

According to an embodiment of the present invention, there is provided a medical image analysis apparatus comprising a reception interface configured to receive at least one first medical image; and at least one processor. The at least one processor is further configured to generate a result of each step of a first process including at least one of an image processing and an image analysis, performed on the at least one first medical image, as at least one of an intermediate result and a final result; generate the final result as a first result image; generate detailed analysis information including the intermediate result and the final result; generate a connection image for the detailed analysis information; and generate at least one second medical image by adding the connection image to the first result image.

The at least one processor may be further configured to perform at least one of a process of storing the at least one second medical image in a first database and a process of transmitting the at least one second medical image to be stored in an external second database.

The at least one processor may be further configured to generate the connection image so that a menu configured to allow a user to edit the at least one second medical image or to generate at least one third medical image in which settings of the at least one second medical image have been adjusted can be connected to the connection image together with the detailed analysis information.

According to an embodiment of the present invention, there is provided a medical image visualization method comprising: acquiring or receiving, by at least one processor, at least one medical image by controlling a reception interface; recognizing, by the at least one processor, a connection image that is presented on the at least one medical image and connects the at least one medical image and detailed analysis information regarding the at least one medical image; acquiring, by the at least one processor, the detailed analysis information, connected to the at least one medical image by the connection image; and visualizing, by the at least one processor, the detailed analysis information on a display, wherein the detailed analysis information includes an intermediate result and a final result of a first process in which an image analysis result of an original medical image is generated as the at least one medical image.

According to an embodiment of the present invention, there is provided a medical image analysis method comprising: acquiring or receiving, by at least one processor, at least one first medical image by controlling a reception interface; generating, by the at least one processor, a result of each step of a first process including at least one of an image processing and an image analysis, performed on the at least one first medical image, as at least one of an intermediate result and a final result; generating, by the at least one processor, the final result as a first result image; generating, by the at least one processor, detailed analysis information including the intermediate result and the final result; generating, by the at least one processor, a connection image for the detailed analysis information; and generating, by the at least one processor, at least one second medical image by adding the connection image to the first result image.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
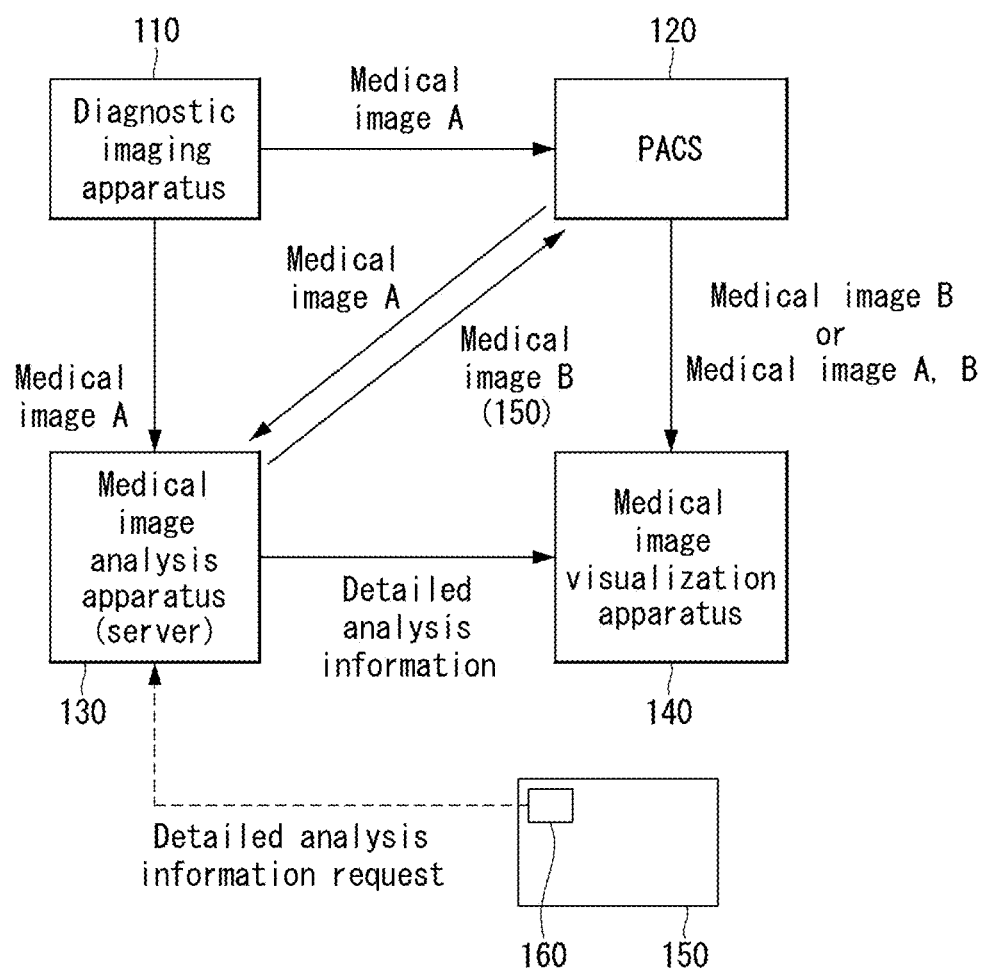
FIG. 1 is a diagram showing a medical image analysis and visualization system including a medical image analysis apparatus and a medical image visualization apparatus according to an embodiment of the present invention.

Other objects and features of the present invention in addition to the above-described objects will be apparent from the following description of embodiments to be given with reference to the accompanying drawings.

The embodiments of the present invention will be described in detail below with reference to the accompanying drawings. In the following description, when it is determined that a detailed description of a known component or function may unnecessarily make the gist of the present invention obscure, it will be omitted.

As to recent medical images such as CT or MRI images, a series of medical images is acquired through a single acquisition process, and the series of medical images is not limited to a single type of lesion but may also be used to detect various types of lesions. For example, for the lungs, a lung nodule as well as chronic obstructive pulmonary disease (COPD) may be diagnosed, emphysema may be diagnosed, and/or chronic bronchitis and/or an airway-related disease may also be diagnosed.

Diagnosis using a medical image refers to a process in which a medical professional identifies a disease or lesion that has occurred in a patient. In this case, prior to diagnosis using a medical image, a medical professional analyzes the medical image and detects a disease or lesion appearing in the medical image. A primary opinion on the detection of a disease or lesion on a medical image is referred to as "findings," and the process of deriving findings by analyzing a medical image is referred to as "reading."

Diagnosis using a medical image is made in such a manner that a medical professional analyzes the findings, derived through the process of reading the medical image, again. In this process, role division is frequently performed in such a manner that a radiologist reads a medical image and derives findings and a clinician derives a diagnosis based on a reading result and the findings.

The assistance of the diagnosis of a medical image has a considerably comprehensive meaning, and may be classified into the case of assisting the process of reading a medical image, the case of assisting the diagnosis of the reading result of a medical image, and the case of assisting decision-making on a medical action such as treatment, administration, or surgery based on the diagnosis result of a medical image.

Furthermore, the case of assisting special medical actions such as treatment, administration, and surgery using a medical image is known as a separate technical field.

Deep learning/CNN-based artificial neural network technology, which has recently developed rapidly, is considered for the purpose of identifying a visual element that is difficult to identify with the human eye when it is applied to the imaging field. The fields of application of the above technology are expected to expand to various fields such as security, medical imaging, and non-destructive testing.

For example, in the medical imaging field, there are cases where a tissue in question is not immediately diagnosed as a cancer tissue in a biopsy state but whether it is a cancer tissue is determined only after being monitored from a pathological point of view. Although it is difficult to confirm whether a corresponding cell is a cancer tissue in a medical image with the human eye, there is an expectation that the application of artificial neural network technology may acquire more accurate prediction results than observation with the human eye.

It is expected that this artificial neural network technology is applied and performs the analysis process of detecting a disease or lesion difficult to identify with the human eye in a medical image, segmenting a region of interest such as a specific tissue, and measuring the segmented region.

The present invention is directed to a technology for assisting the reading and/or diagnosing processes of a medical professional by providing analysis results obtained by the various types of medical image analysis technology to the medical professional. The present invention is characterized by the processes of storing and visualizing the analysis result of a medical image, and these are obtained as means for effectively assisting the reading and/or diagnosis processes of a medical professional.

The present invention relates to an apparatus and method for assisting diagnosis using a medical image. More particularly, the present invention relates to a medical image analysis apparatus and method for automatically analyzing and storing a medical image to assist diagnosis using the medical image, and a medical image visualization apparatus and method for assisting the reading of a medical image by using the analysis result of the medical image.

Since a legacy PACS can store and manage only image data, all analysis information is converted into image data and then provided. Medical image data in a legacy PACS has a limitation in that only an analysis result is provided to a user. Accordingly, although attempts to improve the details of information provided to a user by providing analysis results in a plurality of layers are made in a number of related art documents such as Korean Patent No. 10-1818074 entitled "Artificial Intelligence-based Medical Automatic Diagnosis Assistance Method and System," only image data is still provided even when a plurality of layers is included, so that there is a problem in that a user cannot check a process in which an analysis result is generated.

A user who is a medical professional may have a doubt about or may not be confident with a final result or want to suggest an alternative after checking the final result of image processing and/or image analysis. In this case, the user may want to check whether an intermediate result has been appropriately generated by checking the intermediate result, which is a basis for the generation of the final result.

The recent development of artificial intelligence technology is being extended to a variety of means for obtaining analysis and quantified information on a specific area as well as conventional diagnosis and lesion detection in the field of medical imaging. In this case, there is a demand for a menu configured to allow a medical professional to make clinical determination and decision on the analysis result and quantified information of a medical image provided by artificial intelligence by providing a representative visualization format for the analysis result and quantified information of the medical image. An object of the present invention is to provide a representative visualization format that facilitates the making of clinical determination and decision on artificial intelligence-based medical image analysis and quantification results in response to such a demand.

Meanwhile, the artificial intelligence-based medical image analysis and quantification results are derived through preprocessing such as image segmentation.

In this case, if there is an error during a preprocessing process in a workflow, a subsequent analysis process includes the error. Accordingly, there is a demand for a menu configured to allow a medical professional to make clinical determination and decision on an analysis result by presenting both the analysis result of a medical image and the result of a preprocessing process for deriving the analysis result in a workflow. The present invention is intended to respond to this demand, and an object of the present invention is to visualize artificial intelligence-based medical image analysis and quantification results and also visualize pre-processing results for the provision of the analysis and quantification results in the workflow, thereby assisting a medical professional in making clinical determination and decision.

Among the components of the present invention, the items known to those of ordinary skill in the art prior to the filing of the present application will be described as parts of the components of the present invention in the present specification when necessary. However, if it is determined that a fact obvious to those of ordinary skill in the art may make the gist of the invention obscure, a description thereof may be omitted. In addition, descriptions of the items omitted therein may be replaced by providing notification that the items are known to those of ordinary skill in the art via the related art documents, e.g., Japanese Patent Application Publication No. 2017-182244 entitled "System for Providing Medical Information," U.S. Patent Application Publication No. 2019/0356479 entitled "Method, Server and Communication System for Secure Delivery of Patient's Image and Consent Data," U.S. Pat. No. 10,945,807 entitled "Augmented Reality Viewing and Tagging for Medical Procedures," Korean Patent Application Publication No. 10-2019-0138106 entitled "Picture Archiving and Communication System," Korean Patent No. 10-1818074 entitled "Artificial Intelligence-based Medical Automatic Diagnosis Assistance Method and System," and Korean Patent No. 10-1943011 entitled "Method of Assisting Medical Image Reading of Subject and Apparatus using the same," that are cited therein.

In the above-described related documents, lesion candidates are detected using an artificial neural network and classified, and findings are then generated. Each of the findings includes diagnosis assistance information, and the diagnosis assistance information may include quantitative measurements such as the probability that the finding corresponds to an actual lesion, the confidence of the finding, and the malignity, size and volume of the corresponding one of the lesion candidates to which the findings correspond.

In medical image reading assistance using an artificial neural network, each finding must include numerically quantified probability or confidence as diagnosis assistance information. Since all findings may not be provided to a user, the findings are filtered by applying a predetermined threshold, and only passed findings are provided to the user.

Although Korean Patent No. 10-1943011 entitled "Method of Assisting Medical Image Reading of Subject and Apparatus using the same," etc. disclose a user menu through which a user can adjust a threshold, the same threshold is uniformly applied to all lesions or findings in these related art documents.

Some of the contents disclosed in these related art documents are related to the objects to be achieved by the present invention, and some of the solutions adopted by the present invention are applied to these related art documents in the same manner.

The present invention is directed to an apparatus and method for assisting diagnosis using a medical image. Specifically, the present invention is directed to a medical image analysis apparatus and method for automatically analyzing and storing a medical image to assist diagnosis using the medical image, and is also directed to a medical image visualization apparatus and method for assisting the reading of a medical image by using the analysis result of the medical image. The medical image analysis apparatus and method and the medical image visualization apparatus and method according to the present invention are all implemented by a computing system and software executed in the computing system.

In the following description to be given in conjunction with FIGS. 1 to 18, the descriptions of items that are considered to be well-known techniques widely known in the technical field of the present invention may be omitted as necessary in order to prevent the gist from being obscured, or may be replaced by citing the related art documents.

Furthermore, some or all of the configurations disclosed in the related art documents cited above and to be cited later may be related to some of the objects to be achieved by the present invention, and some of the solutions adopted by the present invention may be borrowed from the related art documents.

Only the items included to embody the present invention among the items disclosed in the related art documents will be considered to be parts of the components of the present invention.

Details of the present invention will be described below with reference to the embodiments of FIGS. 1 to 18.

FIG. 1 is a diagram showing a medical image analysis and visualization system including a medical image analysis apparatus and a medical image visualization apparatus according to an embodiment of the present invention.

Referring to FIG. 1, a medical image A, which is an original medical image acquired from a diagnostic imaging apparatus 110, is transferred to a PACS 120 or a medical image analysis apparatus 130. The PACS 120 is a system for storing the medical image A. The medical image analysis apparatus 130 may receive the medical image A from the diagnostic imaging apparatus 110, or may receive the medical image A stored in the PACS 120 by requesting the medical image A from the PACS 120. The diagnostic imaging apparatus 110 refers to an apparatus for acquiring medical images such as a CT scanner, an MRI scanner and an ultrasound scanner, and the type of diagnostic imaging apparatus 110 may also be referred to as "modality."

The medical image analysis apparatus 130 may be a medical image analysis server. The medical image analysis apparatus 130 may generate detailed analysis information by analyzing the medical image A, which is an original medical image. In this case, the medical image analysis apparatus 130 may generate a medical image B 150 by imaging the analysis results of the medical image A. The medical image analysis apparatus 130 may generate a connection image 160 for the detailed analysis information of the medical image A, and may generate the medical image B 150 including the connection image 160. The medical image analysis apparatus 130 may transmit the medical image B 150 to the PACS 120, and the PACS 120 may store the medical image B 150.

The medical image visualization apparatus 140 may request the medical image A, which is an original image, and/or the medical image B 150, in which the analysis results of the medical image A are generated as an image, from the PACS 120, and may receive the medical image A and/or the medical image B 150 from the PACS 120.

The medical image visualization apparatus 140 may recognize the connection image 160 included in the medical image B 150, and may acquire detailed analysis information connected to the connection image 160. The medical image visualization apparatus 140 may acquire the detailed analysis information by requesting and receiving the detailed analysis information from the medical image analysis apparatus 130. The detailed analysis information may include both image information and non-image information. Since a general legacy PACS can store only image information in conformity with a DICOM format, the medical image B 150 is image information generated to be stored and kept in the PACS 120. The medical image analysis apparatus 130 generates the medical image B 150 by imaging a final result among the detailed analysis results of the medical image A.

Depending on some embodiments of the present invention, when a user accesses the medical image analysis apparatus 130 instead of the medical image visualization apparatus 140, accesses the medical image B, and recognizes the connection image 160 presented on the medical image B, and clicks the connection image 160. Then the medical image analysis apparatus 130 may retrieve the detailed analysis information connected by the connection image 160 from a database thereof, acquire the detailed analysis information, and provide/visualize the detailed analysis information to the user.

Figure 2:
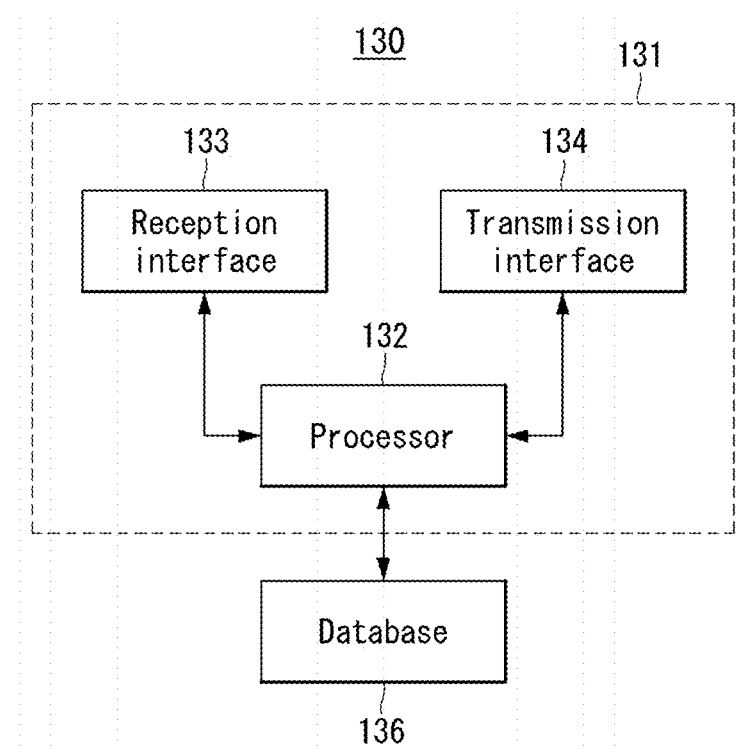
FIG. 2 is a diagram showing an embodiment of the medical image analysis apparatus of FIG. 1.

FIG. 2 is a diagram showing an embodiment of the medical image analysis apparatus of FIG. 1.

Referring to FIG. 2, the medical image analysis apparatus 130 includes a computing system 131, and a database 136. The computing system 131 includes at least one processor 132, a reception interface 133, and a transmission interface 134.

The reception interface 133 may be controlled by the processor 132, and may receive the medical image A from the diagnostic imaging apparatus 110 or the PACS 120. The transmission interface 134 may be controlled by the processor 132 and control the medical image B 150 to the PACS 120, or may transmit the detailed analysis information of the medical image A to the medical image visualization apparatus 140 in response to a request from the medical image visualization apparatus 140.

The database 136 may store the medical image A, the medical image B 150, and the detailed analysis information under the control of the processor 132.

Figure 3:
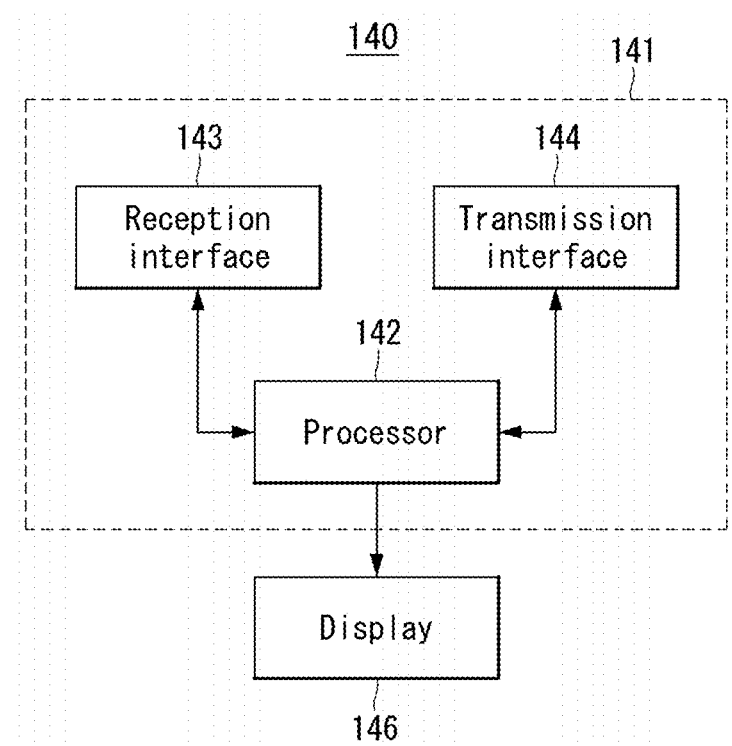
FIG. 3 is a diagram showing an embodiment of the medical image visualization apparatus of FIG. 1.

FIG. 3 is a diagram showing an embodiment of the medical image visualization apparatus of FIG. 1.

Referring to FIG. 3, the medical image visualization apparatus 140 includes a computing system 141, and a display 146. The computing system 141 includes at least one processor 142, a reception interface 143, and a transmission interface 144.

The reception interface 143 may be controlled by the processor 142, and may receive the medical image A and/or the medical image B 150 from the PACS 120. The processor 142 may recognize the connection image 160 presented on the medical image B 150, and may request the detailed analysis information connected to the connection image 160 from a medical image analysis server or the medical image analysis apparatus 130 via the transmission interface 144.

The display 146 may display the medical image A, the medical image B 150, and/or the detailed analysis information under the control of the processor 142.

Figure 4:
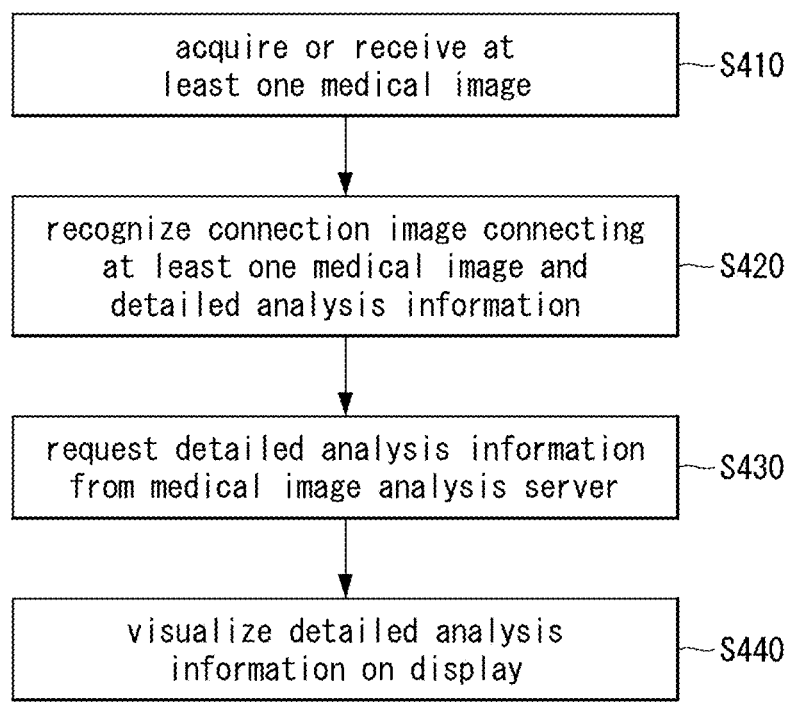
FIG. 4 is an operational flowchart showing a medical image visualization method according to an embodiment of the present invention.

FIG. 4 is an operational flowchart showing a medical image visualization method according to an embodiment of the present invention. The medical image visualization method of FIG. 4 is performed by computer program instructions that are loaded into the processor 142 in the medical image visualization apparatus 140 and executed by the processor 142.

In the medical image visualization method according to the present embodiment, there is performed step S410 of acquiring or receiving, by the at least one processor 142, the at least one medical image B 150 by controlling the reception interface 141.

There is performed step S420 of recognizing, by the at least one processor 142, the connection image 160 that is presented on the at least one medical image B 150 and connects the at least one medical image B 150 and the detailed analysis information of the at least one medical image B 150.

There is performed step S430 of requesting, by the at least one processor 142, the detailed analysis information, connected to the at least one medical image B 150 by the connection image 160, from the medical image analysis server or the medical image analysis apparatus 130.

There is performed step S440 of visualizing, by the at least one processor 142, the detailed analysis information, received from the medical image analysis server or the medical image analysis apparatus 130 on the display 146.

In this case, the detailed analysis information includes the intermediate result and the final result of a process in which the image analysis result of the original medical image (the medical image A) is generated as the at least one medical image B 150.

The detailed analysis information may include image information and non-image information regarding the intermediate result and the final result of the process in which the image analysis result of the original medical image A is generated as the at least one medical image B 150. The at least one medical image B 150 on which the connection image 160 is presented may include only image information in a DICOM format on the assumption that it is stored in a legacy PACS. The connection image 160 may provide a user with the detailed analysis information including non-image information that cannot be stored in the legacy PACS. The connection image 160 is a means for additionally providing the user with detailed analysis information that the user desires to refer to in addition to image information in a DICOM format provided by the PACS 120. In this case, the detailed analysis information may be requested from the medical image analysis apparatus 130, which is a medical image analysis server, by the medical image visualization apparatus 140 via the connection image 160.

The connection image 160 may be included in the medical image B 150 in conformity with a DICOM format as image information, and may be implemented using a QR code, a barcode, or the like that is image information and may include a URL address corresponding to the detailed analysis information.

When the medical image visualization apparatus 140 is a mobile device and there is a separate display device for displaying an image stored in the PACS 120, the mobile device may recognize the connection image 160 by photographing the connection image 160 in the medical image B 150 called from the PACS 120 by using a camera mounted in the mobile device. Additional software may be installed to recognize the connection image 160 of a corresponding region when, in the case where the medical image visualization apparatus 140 is a general personal computer or workstation or in the case where the medical image visualization apparatus 140 is a mobile device and the medical image B 150 is displayed on the mobile device, the region of the connection image 160 of the medical image B 150 displayed on the display 146 of the medical image visualization apparatus 140 is clicked, is selected through the dragging of a mouse, or is touched with the mouse. The additional software may be an add-on program that is installed on the medical image visualization apparatus 140.

The at least one processor 142 may visualize the detailed analysis information together with a user menu configured to allow the user to input feedback on the user's approval for or the rejection of at least one of the intermediate result and the final result of a process in which the image analysis result of the original medical image A is generated as the at least one medical image B 150. The user menu may be provided as a user interface that allows the user to select either one of "confirm" or "reject." According to an embodiment, it may be provided as a user interface that allows the user to select either one of "accept" and "reject." According to another embodiment, a recognition function for the connection image 160 may be activated only when the user selects "reject," and detailed analysis information and/or a work environment menu may be provided to the user by the connection image 160.

When the user approves at least one of the intermediate result and the final result, the at least one processor 142 may store the user's approval for the at least one of the intermediate result and the final result in association with the at least one medical image B 150 and the detailed analysis result in a database. In this case, the database may be the medical image analysis server or the database 136 of the medical image analysis apparatus 130, or may be a database within the medical image visualization apparatus 140. In this case, what is stored is the user's approval, which may be additionally stored as information suggesting that the detailed analysis result is a verified analysis result because it has been approved by a medical professional.

The at least one processor 142 may connect a work environment menu configured to allow the user to manually modify at least one of the intermediate result and the final result with the connection image 160 and provide the work environment menu together with the detailed analysis information. In this case, via the work environment menu, the user may generate new the intermediate result and the final result, corresponding to existing the intermediate result and the final result, independently of the existing the intermediate result and the final result.

The detailed analysis information may include the preprocessing result of the original medical image A as the intermediate result. The quantitative analysis result of the original medical image A generated based on the preprocessing result may be included as the final result. For example, as the image preprocessing result, the segmentation result of an organ and/or lesion obtained by image segmentation may be included in the detailed analysis information as the intermediate result.

The detailed analysis information may include the object identification result of the original medical image A as the intermediate result. A result obtained by filtering the object identification result by applying a threshold thereto may be included as the final result. For example, an object identified as a lesion candidate in computer-aided diagnosis (CAD), i.e., an object identification result, may be included as the intermediate result. The lesion candidate may be objects indicating a specific kind of disease, such as at least one of the lung nodules, tumors, LAA regions indicating COPD, CAC regions, airway wall thickening regions, and so on.

The at least one processor 142 may connect a menu configured to allow the user to edit the at least one medical image B 150 or to generate a new medical image in which the settings of the at least one medical image B 150 are adjusted with the connection image 160, and may provide the menu together with the detailed analysis information.

The at least one processor 142 may connect a work environment menu configured to, when the at least one medical image B 150 is at least one of the reconstructed image and the reformatted image of the original medical image A, generate at least one of new reconstructed image and new reformatted image as a new medical image by adjusting at least one of the range, the angle, the viewpoint, and the option in, at, from, and in which the at least one of the reconstructed image and the reformatted image is generated with the connection image 160, and may provide the work environment menu together with the detailed analysis information.

The at least one processor 142 may connect a work environment menu configured to, when the at least one medical image B 150 includes a report indicative of the image analysis result, generate a new report by adjusting at least one parameter used to generate the report with the connection image 160, and may provide the work environment menu together with the detailed analysis information. For example, a page configured to provide the function of adjusting various parameters/variables used to generate a report, generating a new report, adjusting the number of images captured for a report, and/or adjusting the layout of a report may be provided as the work environment menu.

The at least one processor 142 may connect a work environment menu configured to, when the detailed analysis information includes the object identification result of the original medical image A, allow the user to correct a threshold applied to the object identification result, to generate a result obtained by performing filtering while applying a modified threshold as new detailed analysis information, and/or to manually verify the object identification result before a threshold is applied with the connection image 160, and may provide the work environment menu together with the detailed analysis information. For example, a page configured to change an object for which a filter is applied to an already obtained CAD result or to regenerate a final report by verifying a CAD result may be provided as the work environment menu.

Figure 5:
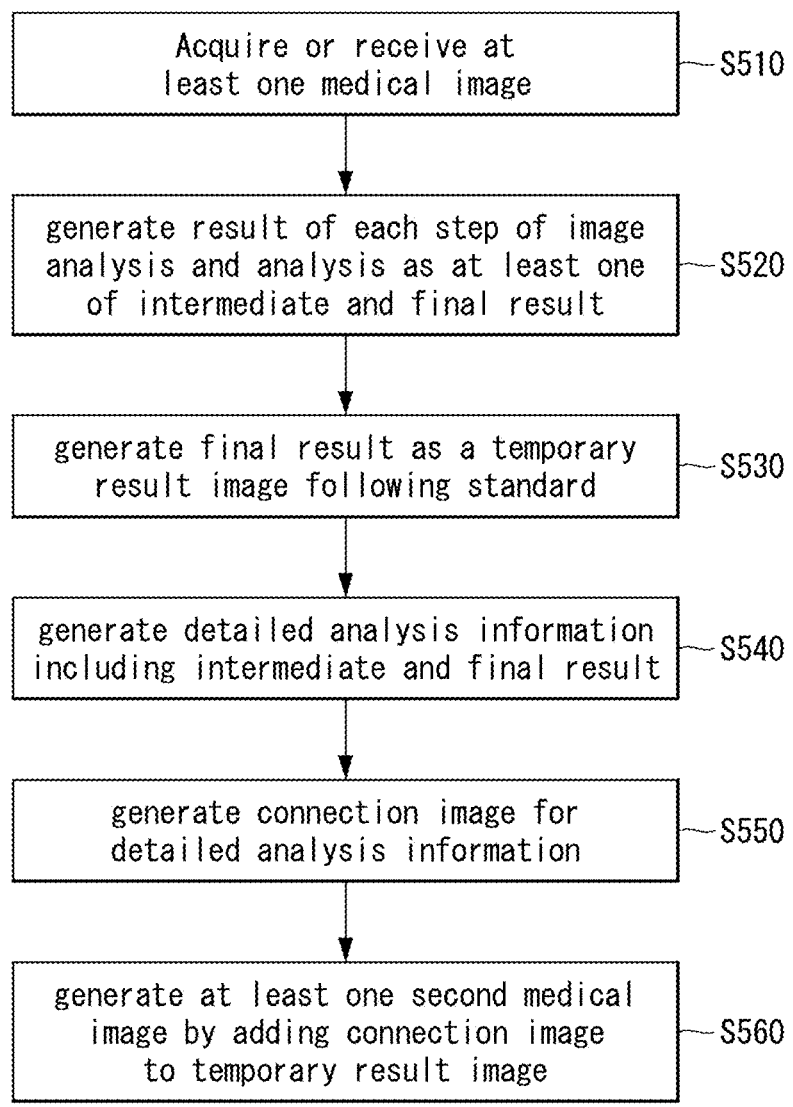
FIG. 5 is an operational flowchart showing a medical image analysis method according to an embodiment of the present invention.

FIG. 5 is an operational flowchart showing a medical image analysis method according to an embodiment of the present invention. The medical image analysis method of FIG. 5 is executed by computer program instructions that are loaded into the medical image analysis server or the processor 132 in the medical image analysis apparatus 130 and executed by the processor 132.

In the medical image analysis method according to the present embodiment, there is performed step S510 of acquiring or receiving, by the at least one processor 132, the medical image A as at least one first medical image by controlling the reception interface 131.

There is performed the step of performing, by the at least one processor 132, an image processing and image analysis process on the at least one first medical image, and there is also performed step S520 of generating, by the at least one processor 132, the result of each step of the image processing and image analysis process, performed on the at least one first medical image, as an intermediate result or a final result.

There is performed step S530 of generating, by the at least one processor 132, the final result as a temporary result image in conformity with a standard (e.g., DICOM).

There is performed step S540 of generating, by the at least one processor 132, detailed analysis information including the intermediate result and the final result.

There is performed step S550 of generating, by the at least one processor 132, the connection image 160 for the detailed analysis information.

There is performed step S560 of generating, by the at least one processor 132, the medical image B 150 as at least one second medical image by adding the connection image 160 to the temporary result image.

There is performed the step of performing, by the at least one processor 132, at least one of the process of storing the medical image B 150 as the at least one second medical image in the first database 136 and the process of transmitting the medical image B 150 via the transmission interface 134 in order to store the medical image B 150 as the at least one second medical image in an external second database. In this case, the external second database may be a database of the PACS 120.

The at least one processor 132 may generate the connection image 160 so that a menu configured to edit the medical image B 150 as the at least one second medical image or to generate at least one third medical image in which the settings of the at least one second medical image are adjusted is connected with the connection image 160 together with the detailed analysis information.

The at least one processor 132 may generate the connection image 160 including a URL linked to a page in which the user's approval/rejection input menu can be presented together with the detailed analysis information. In this case, the user's approval/rejection input menu may be a user menu configured to allow the user to input feedback on the user's approval for or the rejection of at least one of the intermediate result and the final result of a process in which the image analysis result of the original medical image A is generated as the at least one medical image B 150. The user menu may be provided as a user interface that allows the user to select either one of "confirm" or "reject."

When the user approves at least one of the intermediate result and the final result, the at least one processor 132 may store the user's approval for the at least one of the intermediate result and the final result in association with the at least one medical image B 150 and the detailed analysis result in the database 136. In this case, what is stored is the user's approval, which may be additionally stored as information suggesting that the detailed analysis result is a verified analysis result because it has been approved by a medical professional.

The at least one processor 142 may generate the connection image 160 including the URL of a page in which a work environment menu configured to allow the user to manually modify at least one of the intermediate result and the final result is presented together with the detailed analysis information. In this case, via the work environment menu, the user may generate new intermediate result and new final result, corresponding to existing intermediate result and existing final result, independently of the existing intermediate result and the existing final result.

The at least one processor 132 may generate the connection image 160 including a URL linked to a page in which a work environment menu configured to allow the user to edit the at least one medical image B 150 and/or to generate a new medical image in which the settings of the at least one medical image B 150 are adjusted is presented together with the detailed analysis information.

The at least one processor 132 may generate the connection image 160 including a URL linked to a page in which a work environment menu configured to, when the at least one medical image B 150 is at least one of the reconstructed image and the reformatted image of the original medical image A, generate at least one of new reconstructed image and new reformatted image as a new medical image by adjusting at least one of the range, the angle, the viewpoint, and the option in, at, from, and in which the at least one of the reconstructed image and the reformatted image is generated is presented together with the detailed analysis information.

The at least one processor 132 may generate the connection image 160 including a URL linked to a page in which a work environment menu configured to, when the at least one medical image B 150 includes a report indicative of an image analysis result, generate a new report by adjusting at least one parameter used to generate a report is presented together with the detailed analysis information. For example, a page configured to provide the function of adjusting various parameters/variables used to generate a report, generating a new report, adjusting the number of images captured for a report, and/or adjusting the layout of a report may be provided as the work environment menu.

The at least one processor 132 may generate the connection image 160 including a URL linked to a page in which a work environment menu configured to, when the detailed analysis information includes the object identification result of the original medical image A, allow the user to correct a threshold applied to the object identification result, to generate a result obtained by performing filtering while applying a modified threshold as new detailed analysis information, and/or to manually verify the object identification result before a threshold is applied is presented together with the detailed analysis information. For example, a page configured to allow the user to change an object for which a filter is applied to an already obtained CAD result and/or to regenerate a final report by verifying a CAD result may be provided as the work environment menu.

Figure 6:
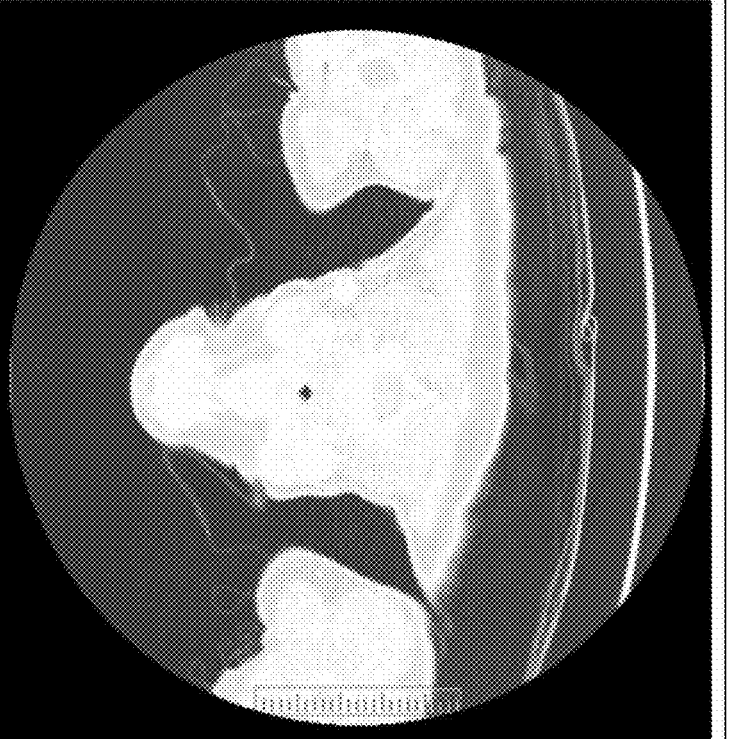
FIG. 6 is a diagram showing a medical image viewer displayed in a medical image visualization apparatus according to an embodiment of the present invention.

FIG. 6 is a diagram showing a medical image viewer displayed in a medical image visualization apparatus according to an embodiment of the present invention.

Referring to FIG. 6, the medical image viewer capable of listing a plurality of studies is shown. In an area 610, a list of a plurality of studies is displayed. One study may include multiple related series.

One study 611 is shown as having been selected in the area 610.

A list of multiple series corresponding to the study 611 is displayed in an area 620. The original medical image A corresponding to a series 0003 622 selected in the area 620 is displayed in an area 630.

The one study 611 may include a plurality of series. In this case, the series 0003 622 may be the original medical image A, a series 0011 is a batch series generated by the image analysis and image processing of the original medical image A, and a series 0087 may be a report on a result obtained by the image analysis and image processing of the original medical image A.

All series provided via the PACS 120 are image information that is implemented in a DICOM format. The medical image analysis apparatus 130 may generate additional information used to support the reading of a medical professional by performing the image analysis and image processing of the medical image A. The additional information may include information obtained by extracting a clinical meaning included in the medical image A, detecting a lesion candidate, or quantitatively measuring a specific region included in the medical image A. Since the DICOM format requires the conversion of the additional information into image information, the user may view only a result converted into image information as a series in the PACS 120.

FIGS. 7 to 14 are views showing examples of detailed analysis information displayed in a medical image visualization apparatus according to an embodiment of the present invention.

As medical image analysis technology develops, image analysis algorithms based on artificial intelligence or artificial neural networks not only detect/diagnose specific lesions in images, but also obtain quantitative information about segmented regions. The process of obtaining such quantitative information is sometimes referred to as measurement. The results of the measurement may serve as information that assists medical professionals in reading images. No matter how accurate image analysis and/or image segmentation is, 100% accuracy cannot be achieved at the current technology level. Furthermore, in medical image analysis, even one failure may lead to a fatal consequence. Accordingly, it is significantly important to prepare an alternative for the failure of image analysis.

If a measurement result is inaccurate or out of a reasonable range, it may be a case where image segmentation, which is a result of a preprocessing process, fails or is inaccurate. Therefore, representative visualization formats may be derived in relation to visualization targets that are a basis or preprocessing results on which a measurement result depends in the present invention.

For example, in a lung image, lung lobe segmentation and airway segmentation are important. Based on these segmentation results, quantitative information related to emphysema and airway wall thickness may be obtained using a medical image analysis algorithm or an artificial neural network.

In a cardiac image, the segmentation of blood vessels such as arteries/veins is important. Based on these segmentation results, quantitative information related to calcium scoring and the like may be obtained using a medical image analysis algorithm or an artificial neural network.

As to the result of the measurement process of obtaining quantitative information, when an image segmentation process, which is a preprocessing process, is not accurate or image segmentation fails, there may be cases where a measurement result exceeds a reasonable range, for example, a quantitative measurement result is excessively low or excessively high.

When the quantitative measurement result is excessively high above the upper limit of a reasonable range, there is a high possibility that a medical professional will check the medical image once more to correct the incorrect measurement. In contrast, a problem may arise when the quantitative measurement result is excessively low below the lower limit of a reasonable range. In this case, when a medical professional refers to only the analysis result of the medical image analysis algorithm or artificial neural network, there is a possibility that the actual disease will be overlooked without being discovered.

However, for the above-described reasons, it will be considerably burdensome for a medical professional to review all the original medical images once again in all cases where quantitative analysis results are provided, and this is completely inconsistent with the purpose of using the quantitative analysis results provided automatically. Accordingly, it would be an effective way of improving workflows and also preventing errors to provide a quantitative analysis result and also provide a user interface that, in order to assist the determination of whether the quantitative analysis result is accurate or there is no error out of a reasonable range in the quantitative analysis result, provides an opportunity to access detailed analysis information by using the connection image 160, visualizes the detailed analysis information together with the quantitative analysis result, and allows a user, who is a medical professional, to check the quantitative analysis result visualized together with the detailed analysis information.

In this case, although the user may be a clinician or radiologist, who is a medical professional, the user may be an assistant staff member who has only knowledge of a sufficient level to check whether a basic preprocessing process such as image segmentation has been performed within a reasonable range depending on an object to be diagnosed. In other words, even when a person does not have clinical knowledge but has representativeness of a sufficient level to check whether the segmentation of a specific region in the image has been accurately performed, he or she may become the user of the present invention.

Furthermore, as shown in the embodiments of FIGS. 1 to 5, it is also important as a workflow to provide a user menu configured to provide assistance such that a correct analysis result can be measured by manually or semi-automatically re-analyzing the analysis result rejected by the user.

It is also important as a workflow to provide the configuration of storing the analysis result approved by the user in a database of the PACS so that it can be used for an original diagnosis purpose (for a diagnosis purpose in a medical institution).

Figure 7:
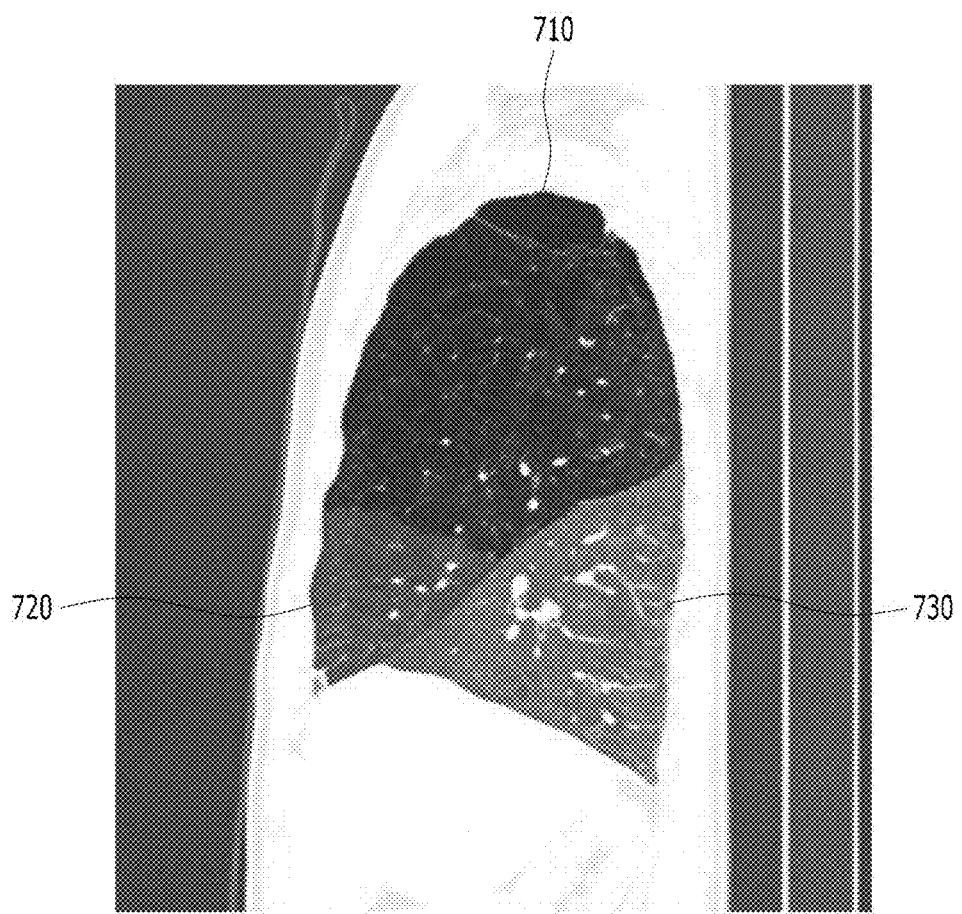
FIG. 7 is a view showing an embodiment of detailed analysis information displayed in a medical image visualization apparatus according to an embodiment of the present invention.

FIG. 7 is a view showing an embodiment of detailed analysis information displayed in a medical image visualization apparatus according to an embodiment of the present invention.

Referring to FIG. 7, there is shown a sagittal image of the center portion of the left lung, which is derived as a representative visualization format as well as detailed analysis information based on the results of lung lobe segmentation and low attenuation area (LAA) analysis.

The sagittal image of the center portion of the left lung is shown together with the result in which the left lung has been segmented into three lung lobes 710, 720, and 730. In this case, the sagittal image of the center portion of the left lung is one of the representative visualization formats according to the analysis result, and the result of the segmentation of the left lung into the three lung lobes 710, 720, and 730 is overlaid and visualized on the sagittal image as a preprocessing result corresponding to or included in the image analysis result.

The LAA is a result of the analysis of a CT image including the lungs, and may mean an area in which a brightness value in the CT image is darker than a reference value. In normal alveoli, the brightness value thereof may change within a CT image depending on the breathing phase. However, an area that is continuously maintained at a brightness value smaller than a specific reference value in the CT image of the lungs is an image filled with air and is considered to have ruptured or inactivated alveoli, and thus the area may be determined to be an area not helpful to breathing.

The quantitative analysis result for the LAA may be represented by the ratio of the volume of regions, in which the brightness value is maintained below a reference value (e.g., −950 HU) within a specific area, to the volume of the corresponding area. Another quantitative analysis result for the LAA may be represented using a method of classifying the sizes of LAA regions and counting and displaying the number of LAA regions for each size. Such a quantification result varies depending on a patient's breathing level (how far the patient breathed). When it is processed using a log calculation, a constant value independent of the breathing level may be obtained and provided as an index for the patient's overall lung capacity. The quantitative measurement result for the LAA may be provided to a user for the diagnosis of chronic obstructive pulmonary disease (COPD) or the like, and may assists diagnosis.

The LAA analysis result is obtained through an image processing process including a plurality of steps.

The lung CT image may be segmented into the whole lung, the left lung, and the right lung. The lung lobes of each of the left and right lungs may be segmented.

A reference area for deriving the ratio of LAA regions for each area in the LAA analysis result may be the segmented lung lobe or left/right lung.

If there is an error in the plurality of preprocessing steps required to derive the LAA analysis result, the reliability of the LAA analysis result may be lowered.

Accordingly, based on the analysis result, the preprocessing results of the plurality of preprocessing steps performed to reach the analysis result may be visualized together with a representative visualization format and provided together with the analysis result.

As described above, FIG. 7 shows an embodiment that may be provided to a user as one of the representative visualization formats for the LAA analysis result based on the LAA analysis result.

Figure 8:
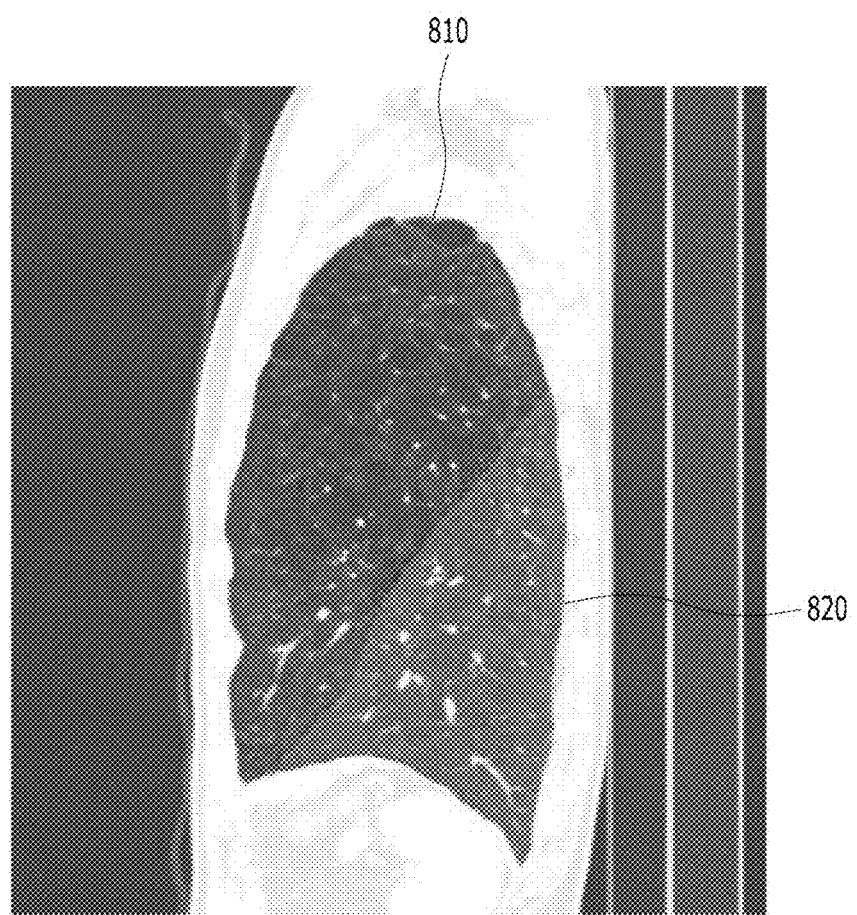
FIG. 8 is a view showing an embodiment of detailed analysis information displayed in a medical image visualization apparatus according to an embodiment of the present invention.

FIG. 8 is a view showing an embodiment of detailed analysis information displayed in a medical image visualization apparatus according to an embodiment of the present invention.

FIG. 8 is a sagittal image of the center portion of the right lung in which there are shown two lung lobes 810 and 820 segmented from the right lung.

FIG. 8 shows the result of a preprocessing process performed to reach the LAA analysis result, which may be an intermediate result before the obtainment of the LAA analysis result. This intermediate result may be provided to a user as one of representative visualization formats as well as detailed analysis information.

Figure 9:
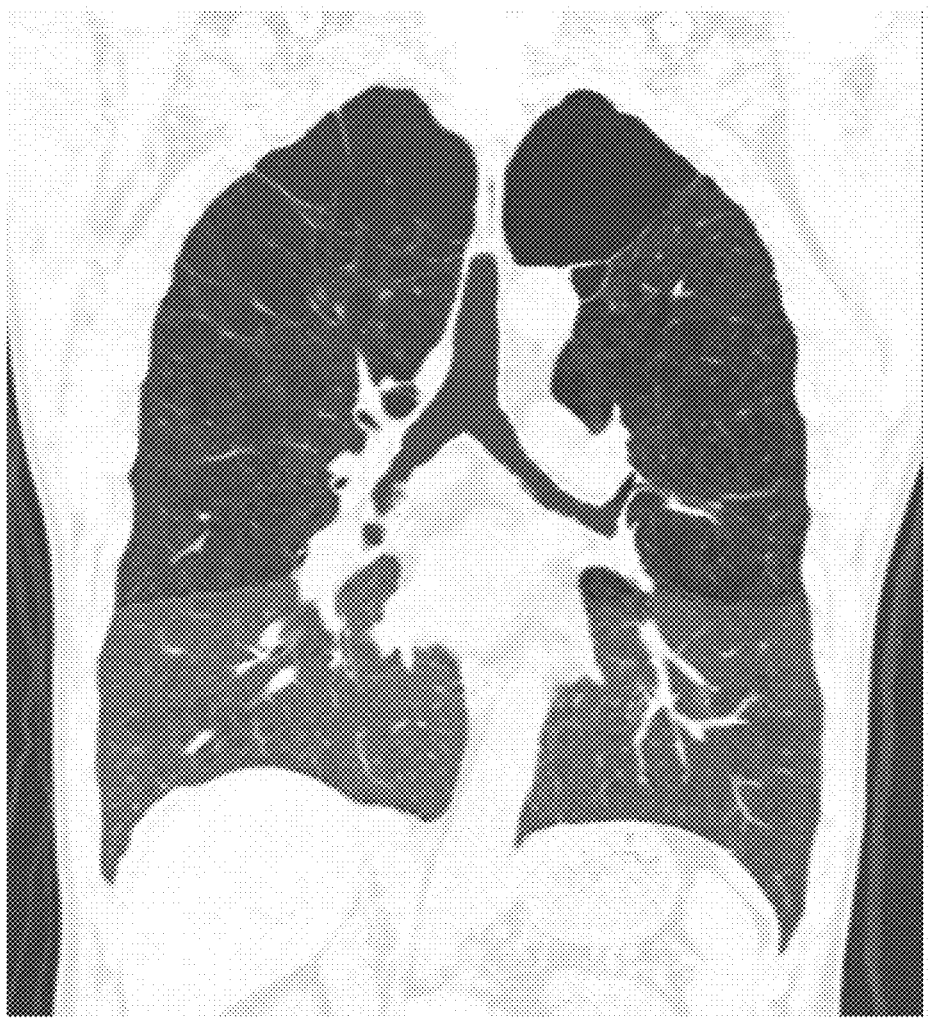
FIG. 9 is a view showing an embodiment of detailed analysis information displayed in a medical image visualization apparatus according to an embodiment of the present invention.

FIG. 9 is a view showing an embodiment of detailed analysis information displayed in a medical image visualization apparatus according to an embodiment of the present invention.

FIG. 9 is a coronal image of tracheal branches, which is one of the representative visualization formats effective for a user to evaluate the result of lung lobe segmentation. In this way, the detailed analysis information may be provided to a user as the representative visualization format effective for a user to evaluate the result of lung lobe segmentation. According to an embodiment of the present invention, instead of FIGS. 7 and 8, FIG. 9 may be provided to the user together with an LAA analysis result. According to another embodiment, all of FIGS. 7 to 9 may be provided to the user together. FIG. 9 may be a visualization format that assists a user in effectively evaluating the result of lung lobe segmentation by representatively visualizing an area where image segmentation is likely to fail rather than showing the overall image segmentation result.

Figure 10:
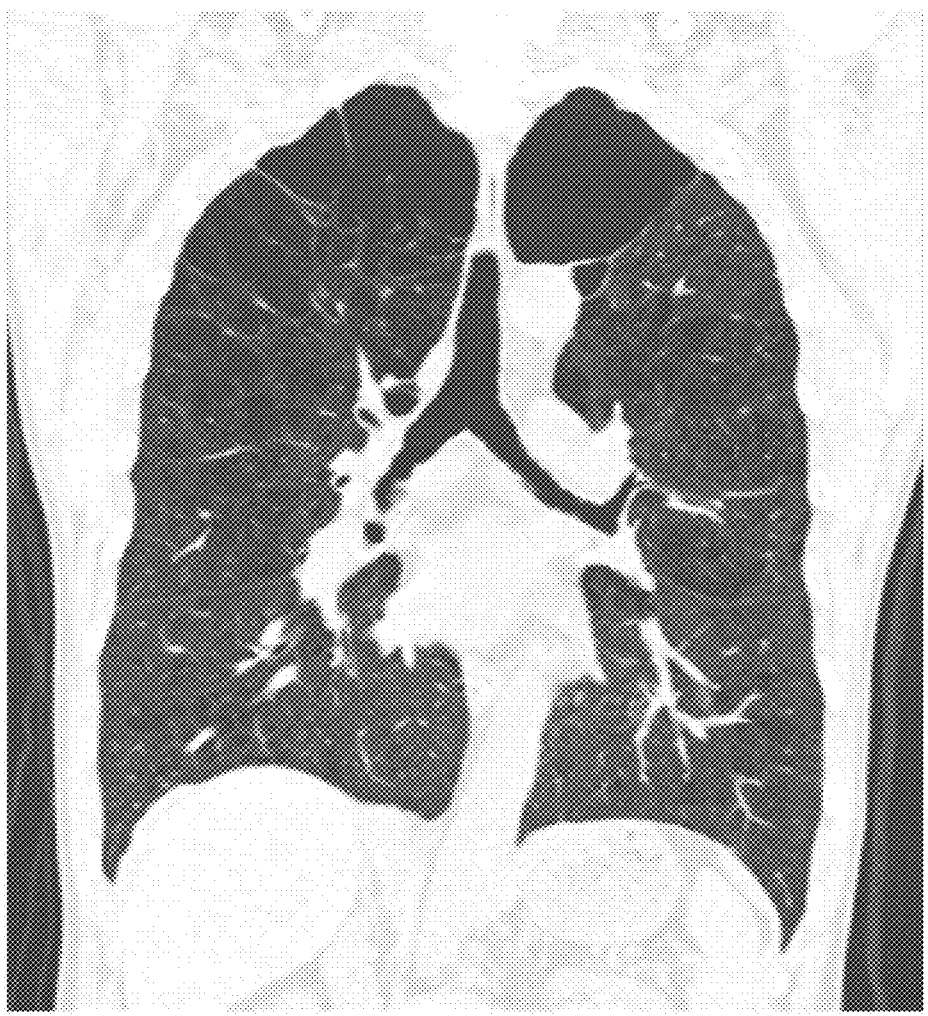
FIG. 10 is a view showing an embodiment of detailed analysis information displayed in a medical image visualization apparatus according to an embodiment of the present invention.

FIG. 10 is a view showing an embodiment of detailed analysis information displayed in a medical image visualization apparatus according to an embodiment of the present invention.

FIG. 10 is one of the representative visualization formats for displaying detected LAA areas on a coronal image of tracheal branches.

Figure 11:
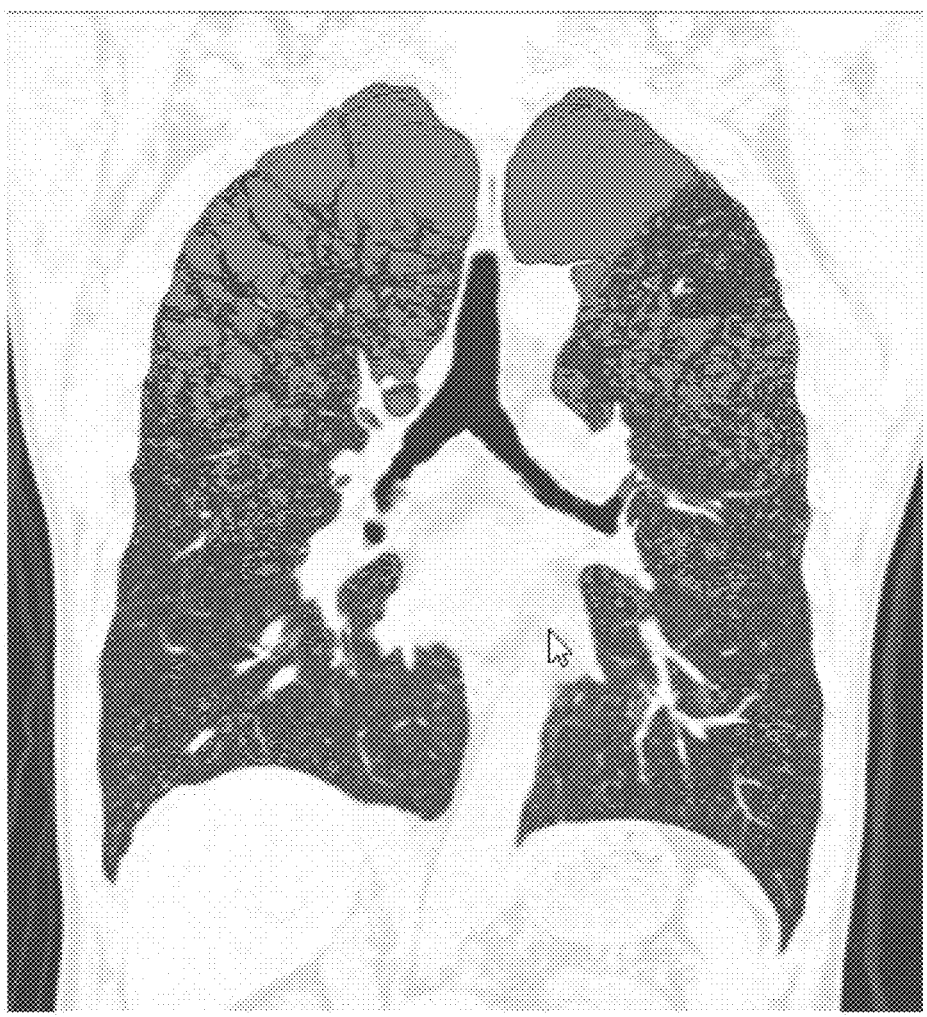
FIG. 11 is a view showing an embodiment of detailed analysis information displayed in a medical image visualization apparatus according to an embodiment of the present invention.

FIG. 11 is a view showing an embodiment of detailed analysis information displayed in a medical image visualization apparatus according to an embodiment of the present invention.

FIG. 11 shows an example in which detected LAA regions, which are an analysis result, are visualized by overlaying the detected LAA regions on the representative visualization image of FIG. 10. When the image of FIG. 11 is displayed together with the analysis result regarding the calculation of the ratio of the LAA regions in a specific area, the medical image reading assistance apparatus of the present invention may assist the user in determining whether the ratio between the left lung/right lung and the portions to be segmented into the lung lobes in the left lung/right lung and the LAA regions in FIG. 11 has been reasonably calculated.

Although not shown in FIG. 11, detected LAA regions may be visualized using visualization elements (color, pattern, and/or brightness) classified based on the sizes of the LAA regions according to another embodiment of the present invention.

Figure 12:
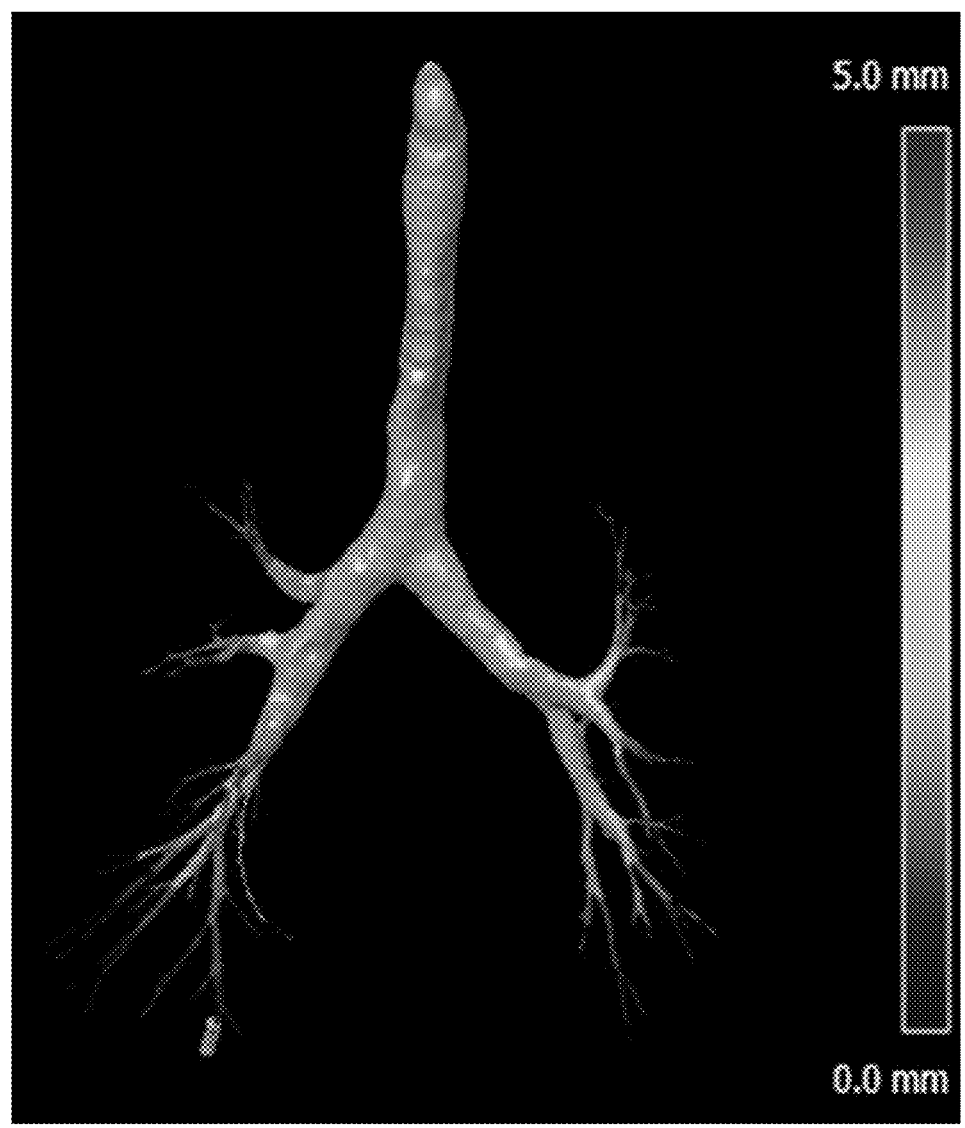
FIG. 12 is a view showing an embodiment of detailed analysis information displayed in a medical image visualization apparatus according to an embodiment of the present invention.

FIG. 12 is a view showing an embodiment of detailed analysis information displayed in a medical image visualization apparatus according to an embodiment of the present invention.

When the analysis result is related to airway segmentation and quantification based on airway segmentation such as airway wall thickness measurement, the airway segmentation may be both an analysis result and a preprocessing result. In this case, a representative visualization format may be generated such that the analysis result and the preprocessing result are included in the representative visualization format together. In FIG. 12, the airway segmentation result of each of the first medical images 150, 250, 350, 450, 550, and 650, which is a preprocessing result, may be represented as a 3D volume rendering image in the frontal direction of the lungs, a visualization element such as color, brightness, saturation, and/or pattern may be added to the 3D volume rendering image, and a quantification result, which is the first analysis result 112, 212, 312, 412, 512, or 612, may be visualized together with the 3D volume rendering image of the first medical image 150, 250, 350, 450, 550, or 650. In this case, each of the first visualization formats 160, 260, 360, 460, 560, and 660 may include the 3D volume rendering image of the first medical image 150, 250, 350, 450, 550, or 650 and the visualization element added thereto. In this case, the first visualization format 160, 260, 360, 460, 560, or 660 may be derived as a representative visualization format that can visualize the information of the first medical image 150, 250, 350, 450, 550, or 650, the preprocessing result, and the first analysis result 112, 212, 312, 412, 512, or 612 together.

In FIG. 12, airway wall thickness measurement analysis values are visualized and displayed together with an airway segmentation result. In this case, the quantitative airway wall thickness information may be visualized and identified with a visualization element such as color, brightness, contrast, pattern, and so on.

A user may determine whether the airway segmentation result is accurate because the user can view the airway segmentation result together with the quantitative analysis result, and the user may receive basis information on whether the quantitative analysis result can be accepted as it is. The user's medical image reading process may be assisted by the medical image reading assistance apparatus of the present invention based on the image of FIG. 12 that is provided as a representative visualization format.

It is known that thickening of the airway wall can make it difficult for a patient to breathe. In general, it is known that the thickness of both the airway lumen and the airway wall is large on the trachea side and the thickness of the airway lumen and the airway wall is smaller toward the microbronchi side. In FIG. 12, a quantification result and a representative visualization format are shown such that the user can determine whether the thickness of the airway wall is appropriately quantified when the relative position thereof in the airway is taken into consideration.

Figure 13:
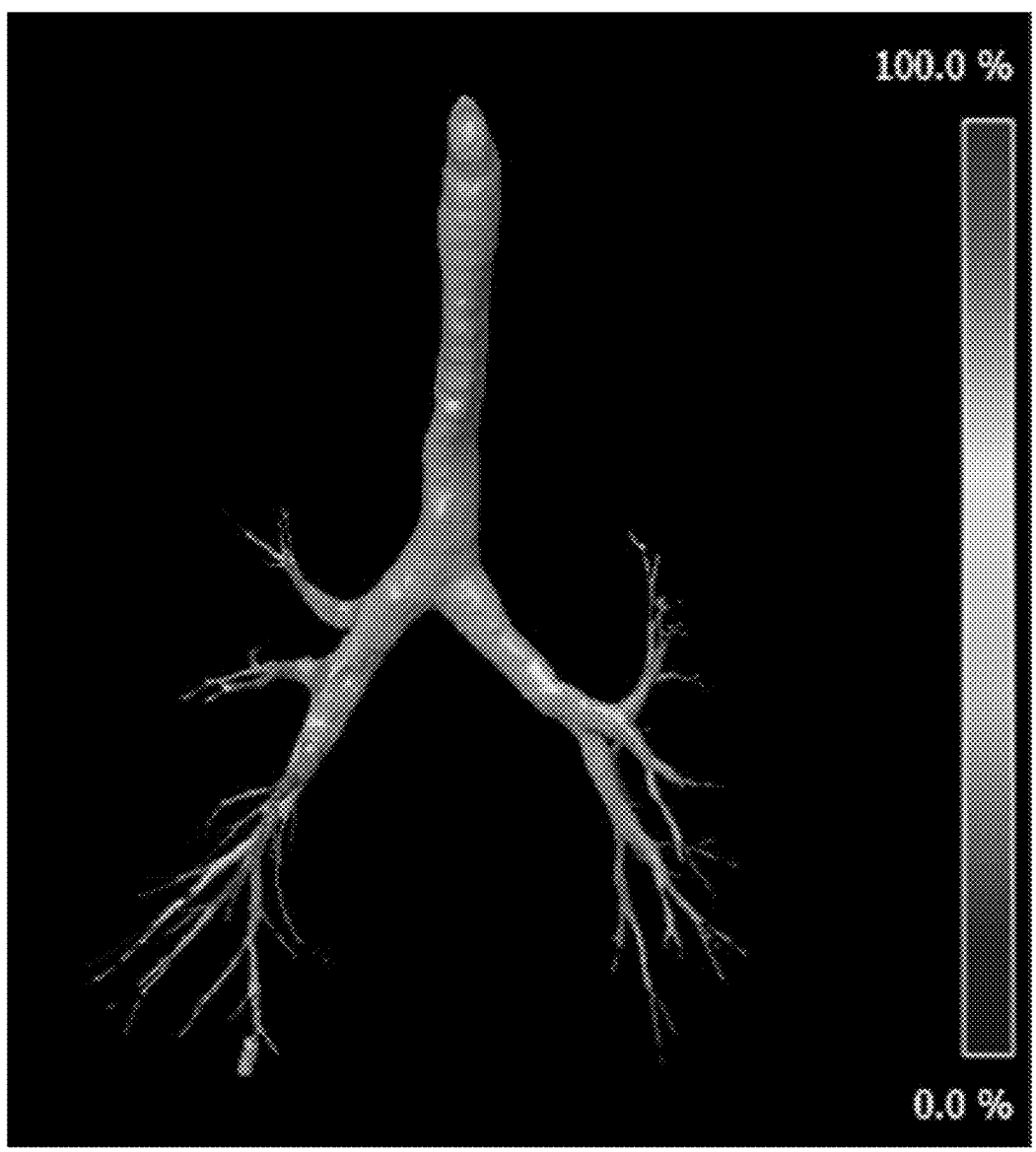
FIG. 13 is a drawing showing an embodiment of detailed analysis information displayed in a medical image visualization apparatus according to an embodiment of the present invention.

FIG. 13 is a drawing showing an embodiment of detailed analysis information displayed in a medical image visualization apparatus according to an embodiment of the present invention.

In FIG. 13, the airway segmentation result and airway wall area % measurement analysis values are visualized and displayed together. In this case, the quantitative airway wall area % information may be visualized and identified with a visualization element such as color, brightness, contrast, pattern, and so on.

As in FIG. 12, a user may determine whether the airway segmentation result is correct because he or she can view the airway segmentation result together with the quantification analysis result, and may receive basis information about whether the quantitative analysis result can be accepted as it is. The user's medical image reading process may be assisted by the medical image reading assistance apparatus of the present invention based on the image of FIG. 13 that is provided as a representative visualization format.

In FIG. 13, the quantification result and the representative visualization format are shown such that the user can determine whether the airway wall area % is appropriately quantified by taking into consideration the relative position thereof in the airway. In addition, for an area where the airway wall area % information thereof is 100% or close to 100%, when the user is a clinician or a radiologist, he or she may diagnose a patient's disease by taking into consideration the analysis result and the representative visualization format visualized in FIG. 13.

Figure 14:
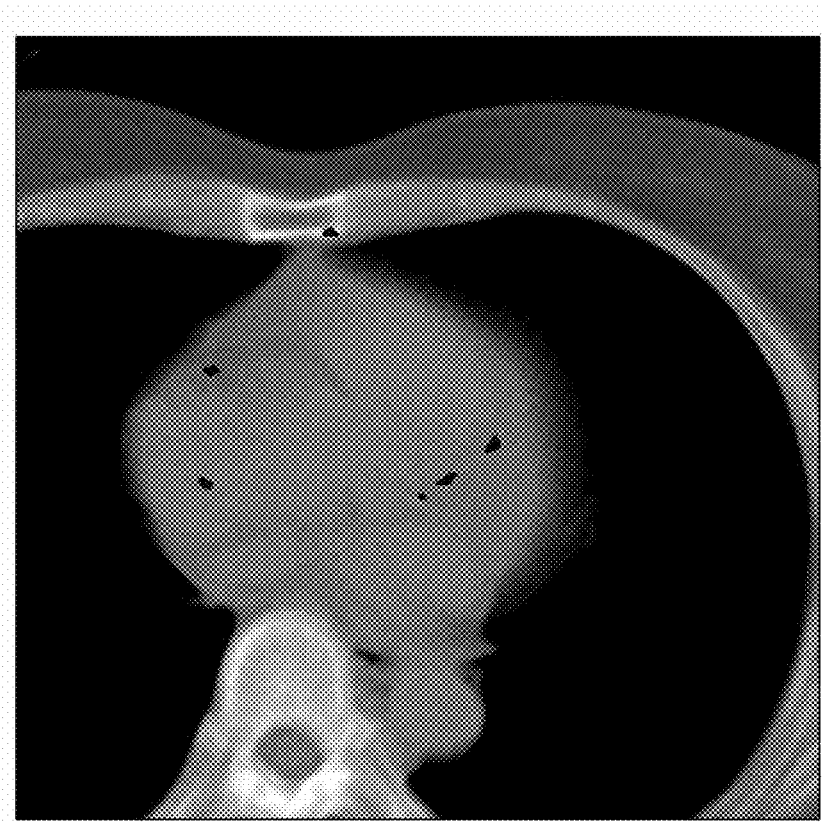
FIG. 14 is a view showing an embodiment of detailed analysis information displayed in a medical image visualization apparatus according to an embodiment of the present invention.

FIG. 14 is a view showing an embodiment of detailed analysis information displayed in a medical image visualization apparatus according to an embodiment of the present invention.

FIG. 14 shows an example of a typical visualization format showing the results of the analysis/measurement of coronary artery calcification (CAC).

When an analysis result is the result of CAC, a cardiovascular segmentation process is performed as a preprocessing process. In this case, when there is an error in the cardiovascular segmentation process and a rib region is incorporated into a blood vessel region, an error in which a CAC measurement value is measured to be much larger than an actual value may occur.

When an analysis result is the result of CAC, a representative visualization format may be provided as an image that allows a user to determine that a bone region on a chest side is incorporated into a blood vessel segmentation region and classified as calcification. For example, one image in which all detected calcification regions are displayed on an axial image in which the slice thickness of a CT image is set to 50 mm may be generated as representative visualization format and visualization information of an analysis result. In this case, the axial image of a CT image (or an MIP image viewed in a direction from a head) is a representative visualization format, and all the detected calcification regions are overlaid on the representative visualization format to generate visualization information.

Figure 15:
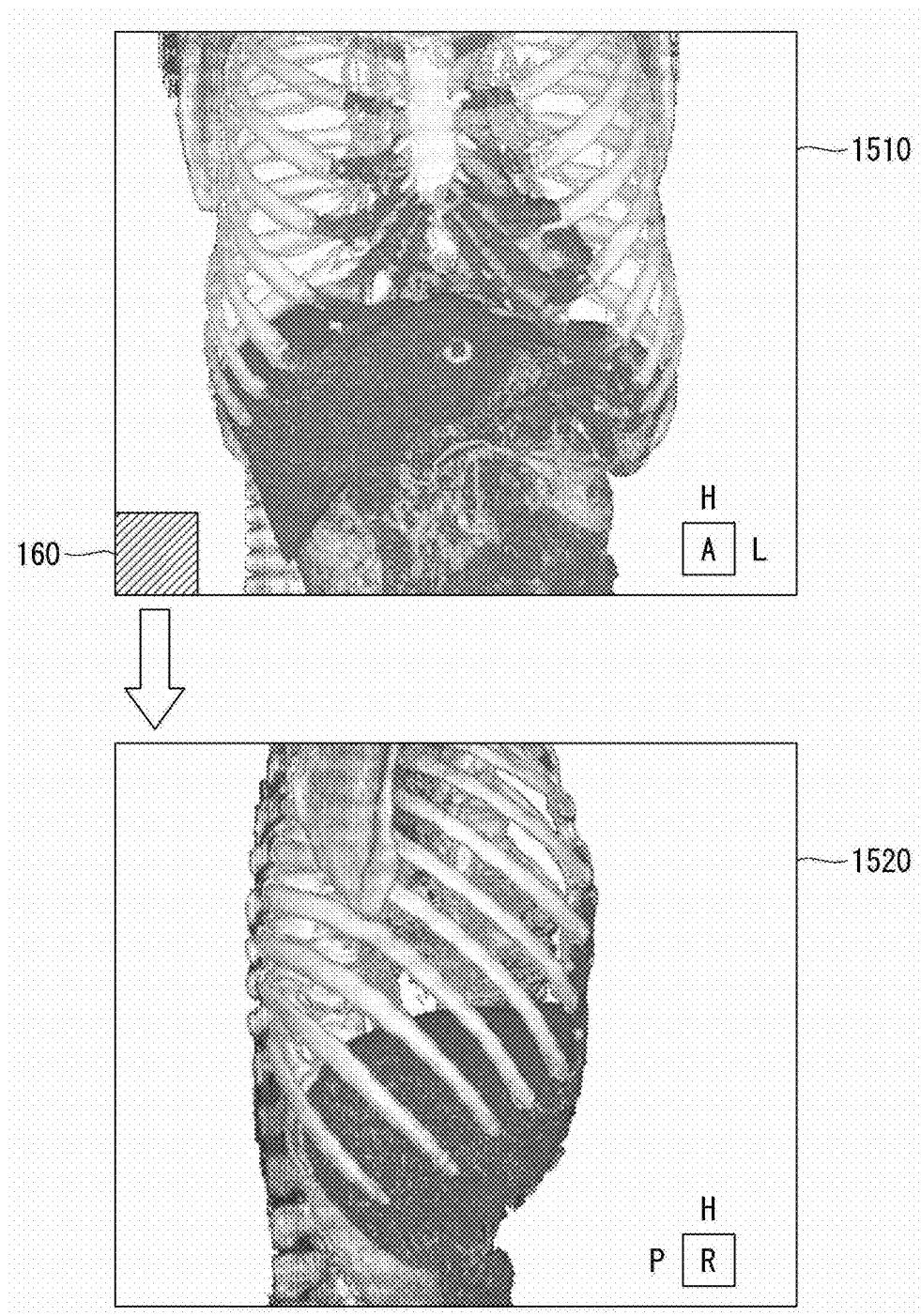
FIG. 15 is a view showing an embodiment of a work environment menu displayed together with detailed analysis information based on a connection image according to an embodiment of the present invention.

FIG. 15 is a view showing an embodiment of a work environment menu displayed together with detailed analysis information based on a connection image according to an embodiment of the present invention.

Referring to FIG. 15, a medical image 1510 in a DICOM format is called and displayed. The medical image 1510 includes the connection image 160. The connection image 160 is recognized, and detailed analysis information related to the medical image 1510 is displayed by the connection image 160. In this case, a work environment menu 1520 is provided as a page configured to change the viewpoint of a reconstructed image of the medical image 1510 by the connection image 160. The work environment menu 1520 may provide the function of changing or regenerating the medical image 1510. The image shown in FIG. 15 is a 3D volume rendering image, and is obtained by reconstructing an original image. The medical image 1510 is a 3D rendering image that has already been reconstructed. When a user determines that the medical image 1510 is insufficient to diagnose a lesion or disease of a patient, he or she may call the work environment menu 1520 that has generated the medical image 1510 by using the connection image 160. Since the work environment menu 1520 includes non-image information, it may not be provided by the PACS 120, and may be transferred to the user's medical image visualization apparatus 140 in the state of being stored in an analysis server, such as the medical image analysis apparatus 130, or a cloud server. In this case, the user may perform the 3D rendering of the medical image 1510 again, may change the direction, viewpoint, and/or the like of the 3D rendering image, and may reconstruct the axial image into a sagittal or coronal image or reconstruct/reformat the image in an oblique direction by using the work environment menu 1520.

Figure 16:
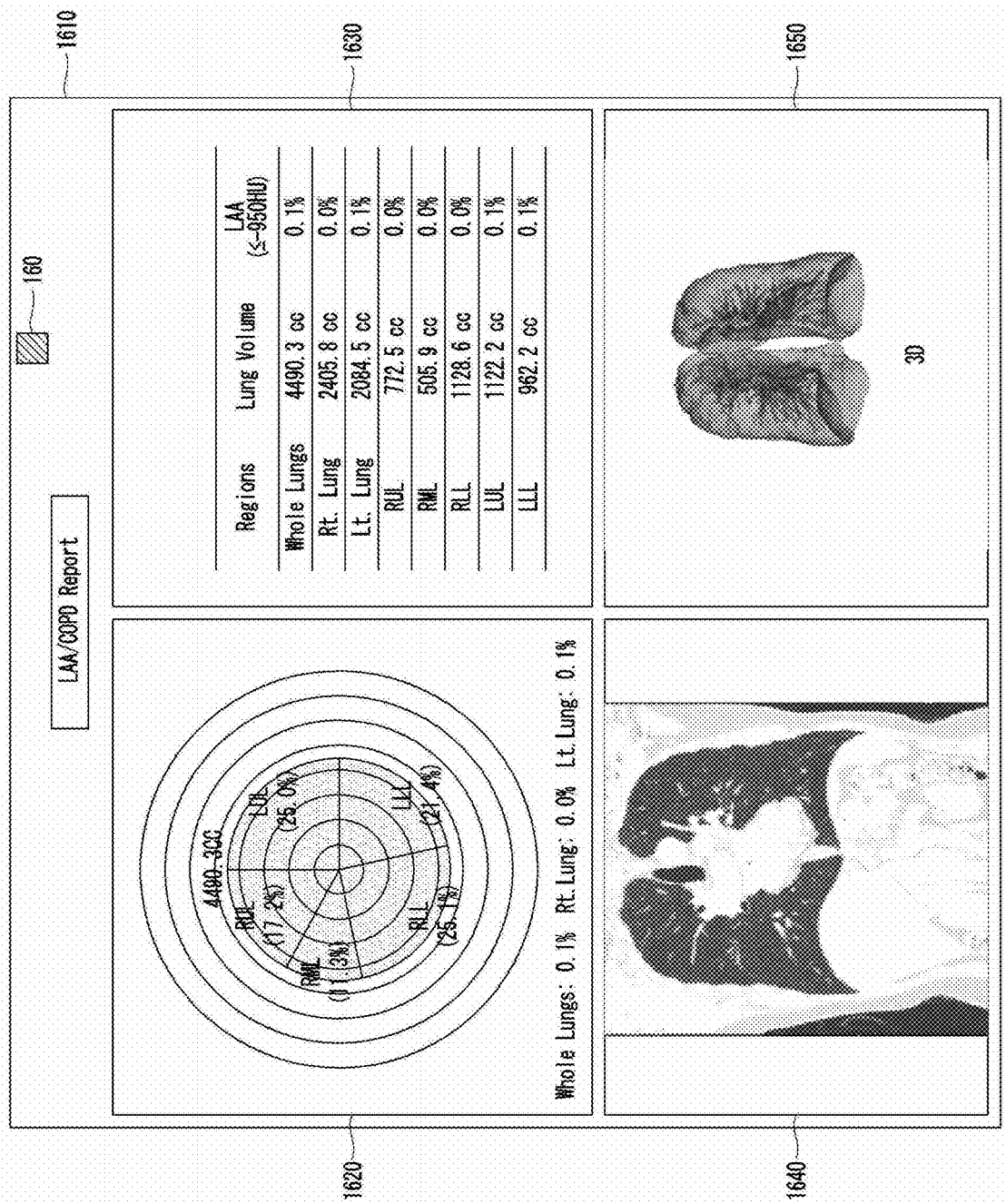
FIG. 16 is a view showing an embodiment of detailed analysis information displayed based on a connection image according to an embodiment of the present invention.

FIG. 16 is a view showing an embodiment of detailed analysis information displayed based on a connection image according to an embodiment of the present invention.

In FIG. 16, a report configured to summarize the image analysis and image processing results of the medical image A is introduced as an embodiment of the detailed analysis information. The medical image analysis apparatus 130 generates the medical image B 150 by capturing the image analysis and image processing results of the medical image A as an image. The connection image 160 may be presented on the medical image B 150, as shown in FIG. 16.

The overall frame 1610 of the medical image B 150 is provided to a user as a report 1610 including the processing, analysis, and measurement results of the medical image A. Although an embodiment in which the one connection image 160 is displayed in the overall frame 1610 is shown in FIG. 16, each connection image (not shown) may be displayed in each frame area 1620, 1630, 1640, or 1650 of the medical image B 150 according to another embodiment of the present invention.

The detailed analysis information connected by the connection image 160 may be provided to the user together with a work environment menu configured to generate the intermediate result and the final result of each frame area 1620, 1630, 1640, or 1650 of the report 1610 on the medical image B 150.

The user may be provided with a page configured to allow the user to sequentially view the detailed analysis information of the frame areas 1620, 1630, 1640, and 1650 via the connection image 160. For example, the frame area 1620 in which the quantitative measurement results of the medical image A are summarized and graphed and the frame area 1630 in which results are summarized as a table may be provided as the detailed analysis information.

The medical image (a scout image or coronal image) that is a basis for the generation of the frame area 1620 and the frame area 1630 may be provided as the frame area 1640. In this case, a reconstructed image of a region of interest (ROI) may be provided to the frame area 1650 through image processing (image segmentation, image reconstruction, and/or the like) in the frame area 1640.

In the medical image B 150 and report 1610 provided as DICOM images, only the image information formed by capturing already generated detailed analysis information is provided. Accordingly, when the user has a doubt about or may not be confident with the process of obtaining the detailed analysis information or wants to re-verify the overall process of obtaining the detailed analysis information, the DICOM image alone may not provide information about the overall process of obtaining the detailed analysis information. The present invention may provide a work environment menu configured to provide non-image information as well as DICOM images by providing a separate link to detailed analysis information so that the user can view the overall process of obtaining the detailed analysis information, can modify or change it as necessary, and can attempt to regenerate detailed analysis information.

For example, in the frame area 1640, a work environment menu for the original medical image A of the frame area 1640 may be connected, and the work environment menu may be provided by the user's selection. The user may attempt to newly generate the overall content of the report 1610 by adjusting various parameters or variables selectable in the frame area 1640. In addition, when the report 1610 includes a reconstructed image as shown in FIG. 16, the work environment menu may be used to adjust the number of images to be captured for the report 1610 or to additionally capture an image to be included in the report 1610. In other words, when only a coronal image of the front is included in the report 1610 but only the coronal image is considered to be insufficient, the user may generate a new report by adding an oblique view, a sagittal view, and/or the like.

A report newly generated by adjusting parameters or variables by the user or adding an image may be transmitted back to the PACS 120 by the image analysis apparatus 130. In this case, the new report is image information captured in a DICOM format, and may be additionally stored in the PACS 120 as a new series in the patient's existing study 611.

According to an embodiment, the report 1610 provided by the present invention may include a structured report (SR).

Figure 17:
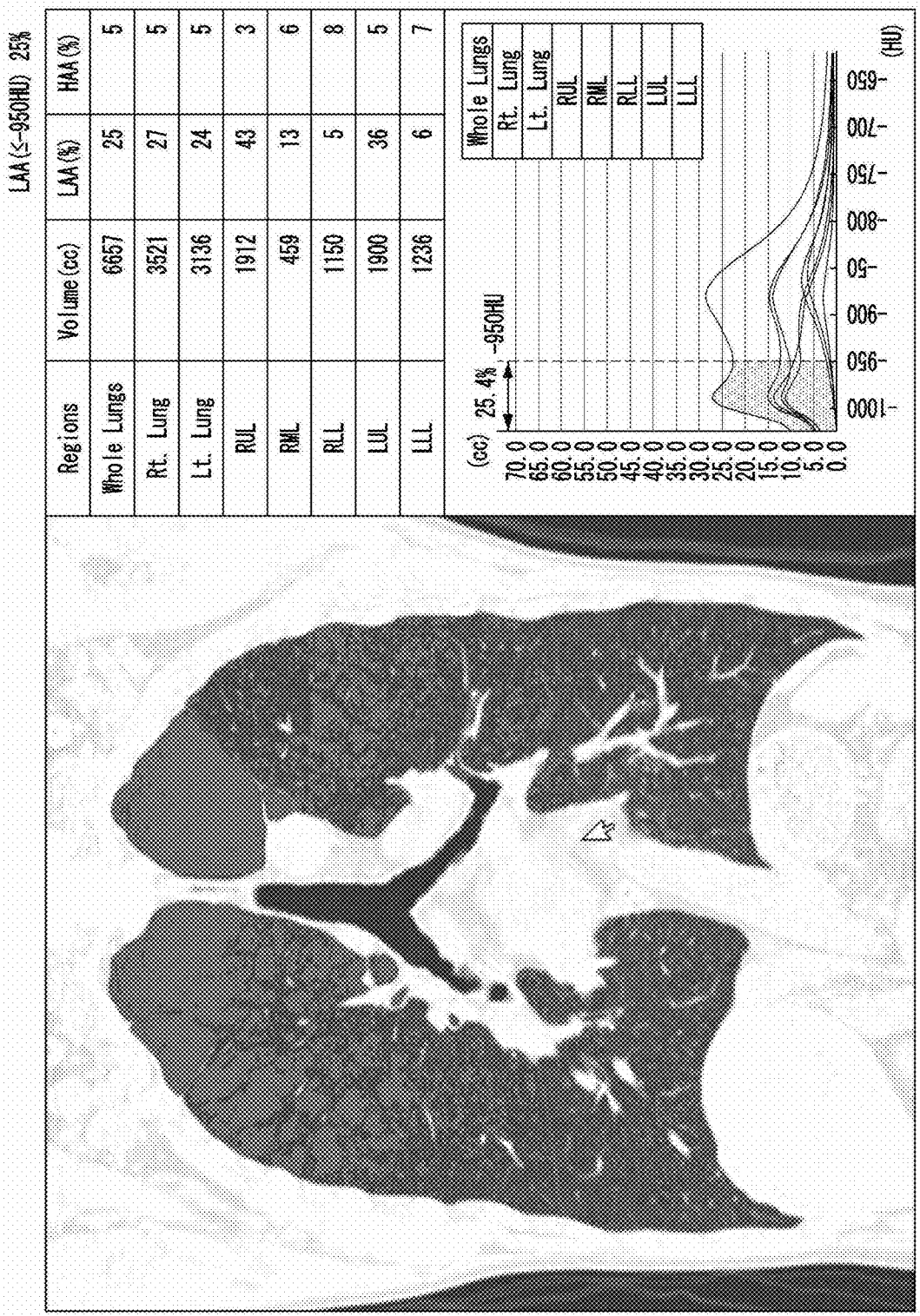
FIG. 17 is a view showing an embodiment of detailed analysis information and a work environment menu displayed together based on a connection image according to an embodiment of the present invention.

FIG. 17 is a view showing an embodiment of detailed analysis information and a work environment menu displayed together based on a connection image according to an embodiment of the present invention.

Figure 18:
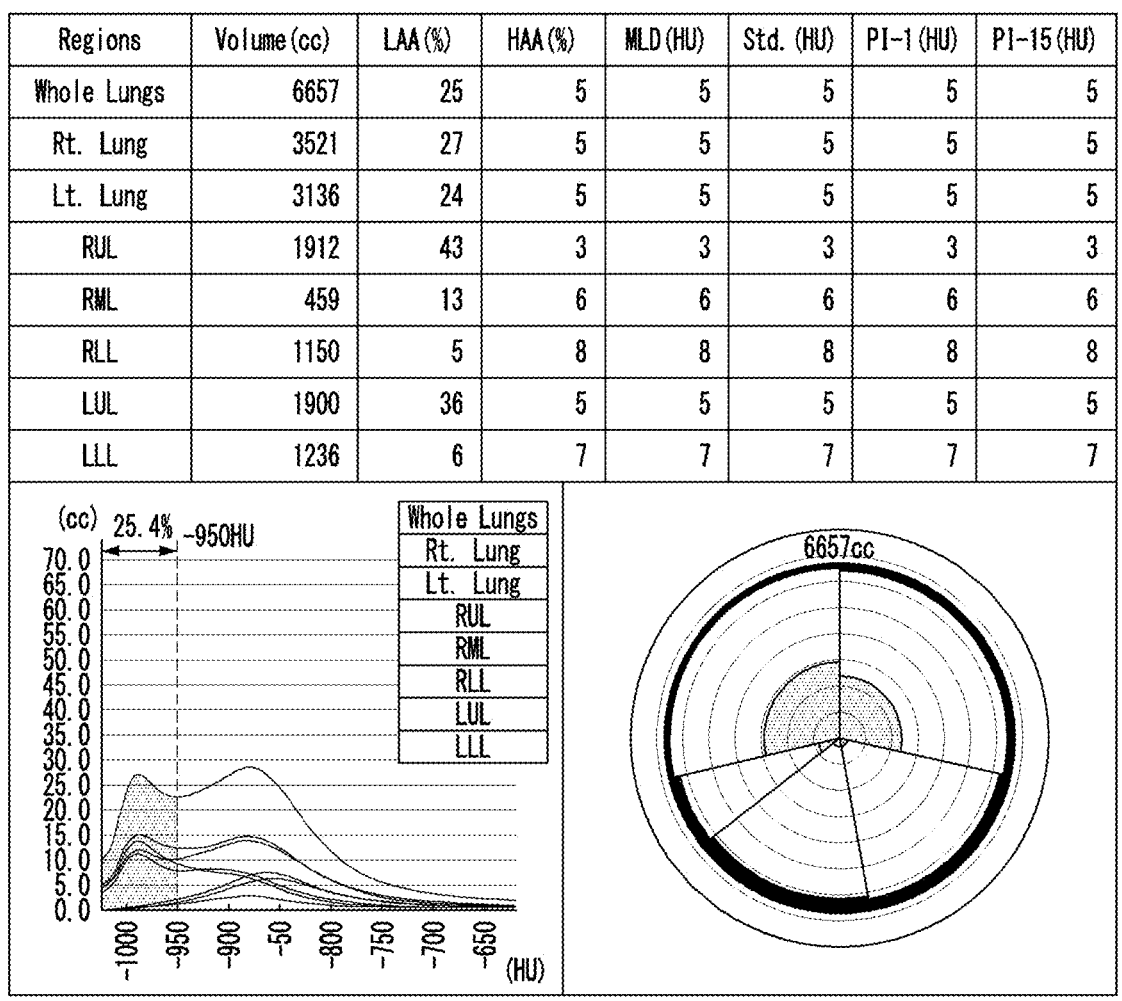
FIG. 18 is a view showing an embodiment of detailed analysis information and a work environment menu displayed together based on a connection image according to an embodiment of the present invention.

FIG. 18 is a view showing an embodiment of detailed analysis information displayed together based on a connection image according to an embodiment of the present invention.

When the medical image B 150 provided in a DICOM format is the result of a computer-aided diagnosis (CAD), the detailed analysis information of the medical image B 150 may be called from the medical image analysis server or the medical image analysis apparatus 130 and displayed via the connection image 160 that is presented on the medical image B 150.

FIG. 17 shows an embodiment of detailed analysis information and a work environment menu connected by the connection image 160 for a CAD result.

The CAD result includes the identification result of an object in the medical image A or the quantitative measurement result of an object in the medical image A. For example, the left part of FIG. 17 shows identified LAA region information which results from the medical analysis or CAD overlayed on the segmentation of the lung area. The upper right part of FIG. 17 shows a table includes regional volume information of each lung part segmented, LAA area % identified for each lung part segmented, and HAA (High attenuation area) area % identified for each lung part segmented as an example of CAD result. The lower right part of FIG. 17 shows a histogram of pixels included in each lung part segmented, and especially how many pixels is counted as LAA region for each lung part segmented, as another example of CAD result. When the user has a doubt about or may not be confident with the CAD results, the medical image visualization apparatus 140 may request detailed analysis information from the medical image analysis server or the medical image analysis apparatus 130 in response to a user input corresponding to the connection image 160, may receive the analysis information, and may display it on the display 146.

In this case, a work environment menu may be provided together with the detailed analysis information. The user may adjust a threshold for the object identification result or quantitative measurement result of the CAD result, may change an object to be viewed by applying a filter to the CAD result, or may reset and verify a CAD result.

In this case, an image segmentation result obtained by artificial intelligence/an artificial neural network or the like may be used as a preprocessing result before the obtainment of the CAD result. When the image preprocessing result, such as the image segmentation result, obtained by the artificial neural network is not satisfactory, the work environment menu may provide a menu configured to allow the user to manually modify the image preprocessing result such as an image segmentation result.

In this case, a new analysis result obtained through the user's change, correction, and re-verification is captured as a DICOM image and generated as a new report image. The new report image may be transmitted back to the PACS 120 by the image analysis apparatus 130. In this case, the new report is image information captured in a DICOM format, and may be additionally stored in the PACS 120 as a new series in the patient's existing study 611.

The upper part of FIG. 18 shows a further detailed example of table includes regional volume information of each lung part segmented, such as identified area % information of LAA, HAA, MLD, Std, PI-1, PI-15 regions. The lower left part of FIG. 18 shows a histogram of pixels included in each lung part segmented, as another example of CAD result. The lower right part of FIG. 18 shows a radial graph indicating relative occupied volume ratio of LAA area to the entire volume for each lung part segmented, and relative occupied volume ratio of each lung part segmented to the whole lung volume. For example, the radial graph of FIG. 18 shows RUL (Right Upper Lobe) and LUL (Left Upper Lobe) have two largest volumes relative to other lung part segmented. Further, the radial graph of FIG. 18 shows that RUL and LUL regions have the highest LAA area % and the largest volumes counted as LAA regions.

The detailed analysis information connected by the connection image, such as a QR code, includes the intermediate result and the final result of a process in which the image analysis result of the original medical image (the medical image A) is generated as the at least one medical image B.

The at least one medical image B to which the QR code is assigned includes only the final result (to be stored in a Legacy PACS), and does not include the intermediate result. In other words, the present invention is characterized by providing the intermediate result before the obtainment of the final result using a QR code or the like when the user checks the at least one medical image B generated as the final result and then wants to verify in detail the process of obtaining the final result.

In this case, both the final and intermediate results are results of each step performed by the image preprocessing process, the image processing process, and/or the image analysis process for the original medical image. The present invention is targeted at cases where it is impossible to verify the appropriateness of a medical image or a final result only with a patient's medical record related to the corresponding medical image provided in connection with a QR code on the medical image and the patient's personal information, in known technologies such as the technology disclosed in Korean Patent Application Publication No. 10-2019-0138106. Accordingly, it may be possible to provide information and a work environment that allow a user who is a medical professional to verify in detail the overall process ranging from the original medical image to the final result.

The reason why it is difficult to provide an intermediate result to a user from the beginning is that such an intermediate result frequently has a huge amount of data or contains detailed information that cannot be handled with image data alone that can be provided by the legacy PACS.

The legacy PACS stores and manages only DICOM-based image data, and additional information other than image data is managed in databases other than Legacy PACS, such as electronic medical records (EMRs) and a clinical information system (CIS). However, EMRs or a CIS can only store and manage data complying with predefined regulations, and cannot store and manage information deviating from the regulations. Accordingly, the intermediate result mentioned in connection with the present invention can neither be provided to the user by the conventional legacy PACS not by EMRs, a CIS, etc., and needs to be provided through separate image analysis software.

In this case, the user may want to check only the intermediate result required by him or her instead of executing image analysis-dedicated software every time, and the present invention may provide at least one intermediate result related to the final result to the user as detailed analysis information by using a QR code or the like. The user may relatively easily check the intermediate result, which corresponds to a step prior to the final result, even without directly executing the image analysis-dedicated software, and may be provided with abundant information used to determine whether the final result is appropriate.

A user who is a medical professional may have a doubt about or may not be confident with a final result or want to suggest an alternative after checking the final result of image processing and/or image analysis. In this case, the user may want to check whether an intermediate result has been appropriately generated by checking the intermediate result, which is a basis for the generation of the final result.

In this case, it may be insufficient if the intermediate result is provided to the user only in the form of an image. The user may often determine whether the intermediate result is appropriate only when a menu through which the user can interactively check each of the objects and/or values included in the intermediate result is additionally provided. Accordingly, the present invention is characterized by being configured to provide the user with a menu, through which the user can interactively check each of the objects and/or values of the intermediate result obtained during the processing process of the computer software, via the connection image.

A user who is a medical professional may have a doubt about or may not be confident with an intermediate result or want to suggest an alternative after checking the intermediate result. The user may want to obtain a new intermediate result by changing the characteristic settings or threshold of the intermediate result and then obtain a new final result from the new intermediate result. The present invention is characterized by being configured to provide a work environment and user menu configured to allow the user to generate a new intermediate result by changing a characteristic setting or value required for the generation of an intermediate result so that the intermediate result obtained in a processing process of computer software can be newly obtained.

A user who is a medical professional may want to newly adjust a final result by using a new intermediate result. Alternatively, a user who is a medical professional may want to adjust only a final result while using an existing intermediate result without change. The present invention is characterized by being configured to provide a work environment and user menu configured to allow the user to generate a new final result by changing a characteristic setting or value required for the generation of a final result so that the final result obtained during a processing process of computer software based on the intermediate result can be newly obtained.

In this case, even when a user is provided with a work environment that allows a user to generate a new intermediate result or final result, the user may perform only a function required by him or her on his/her computing terminal without directly executing the overall image analysis-dedicated software. This advantage of the present invention can provide an interface that allows a user to freely test a new intermediate result or final result in a mobile terminal, a wearable terminal, or a computing terminal with deteriorated computing power/memory performance.

The visualization of an intermediate result or a work environment that allows the generation of a new intermediate/final result may be provided to a user by means of thin-client technology. In this case, the user's computing terminal is operated using only the minimum resources required for visualization or the driving of the work environment (the generation of a new intermediate result/final result), and the calculation required for visualization or the generation of a new intermediate result/final result may be performed on a cloud-based computing server.

The data derived or obtained as a result in the visualization of the detailed analysis information of the present invention and the generation of a new intermediate result/final result may be stored in a cloud-based database server.

According to the present invention, in a workflow for a clinician or radiologist, the clinician or radiologist as a user may identify an intermediate result, which is a basis for the generation of a final result, and may determine whether the intermediate result and a final result resulting therefrom have been appropriately generated.

According to the present invention, in a workflow for a clinician or radiologist, there may be provided the representative visualization format that is appropriately designed for the clinician or radiologist to make determination or decision on an artificial intelligence-based image analysis result.

According to the present invention, there may be provided the medical image analysis results and quantification results based on the artificial intelligence. Further, there may be provided the pre-processing results for providing the analysis results and the quantification results in workflow may be visualized together with the analysis results and the quantification results, therefore, the medical professionals may be assisted regarding the clinical diagnosis and/or decision.

According to the present invention, when the medical professionals reject the medical image analysis results and the quantification results based on the artificial intelligence, the medical professionals may investigate the pre-processing results which is a basement of the medical image analysis results and the quantification results, may reject the pre-processing results, and may perform again the pre-processing, analysis, and quantification process independently of the artificial intelligence.

According to the present invention, there may be provided a user menu to user via connected image, wherein the menu may allow user to check interactively objects and/or values from intermediate results generated during the processing by the computer software (program command/instruction) which is loaded to and executed by processors.

According to the present invention, there may be provided a user menu and/or work/job environment to user via connected image, wherein the menu and/or work/job environment may allow user to generate a new intermediate result by modifying the special settings and/or parameters needed to generate the intermediate result which is generated during the processing by the computer software (program command/instruction).

According to the present invention, there may be provided a user menu and/or work/job environment to user via connected image, wherein the menu and/or work/job environment may allow user to generate a new final result by modifying the special settings and/or parameters needed to generate the final result which is generated from the processing by the computer software (program command/instruction).

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

What is claimed is:

1. A medical image visualization apparatus comprising:
   a reception interface configured to receive at least one medical image;
   at least one processor; and
   a display,
   wherein the at least one processor is configured to:
      recognize a connection image that is presented on the at least one medical image and connects the at least one medical image and detailed analysis information regarding the at least one medical image;
      acquire the detailed analysis information, connected to the at least one medical image by the connection image; and
      visualize the detailed analysis information on the display,
   wherein the detailed analysis information includes an intermediate result of a first process, in which the intermediate result is generated based on an original medical image, and a final result of a second process, in which the final result is generated at least based on the intermediate result, and the at least one medical image is generated by imaging the final result,
   wherein the at least one medical image includes the final result including at least one of a finding result, a diagnosis result, a threshold-based filtering result, or a quantified analysis result related to at least one region or object, and
   wherein the intermediate result includes at least one of a segmentation result or an identification result of the at least one region or object, as a preprocessing result of the final result.

2. The medical image visualization apparatus of claim 1, wherein the detailed analysis information includes image information and non-image information regarding the intermediate result of the first process and the final result of the second process.

3. The medical image visualization apparatus of claim 1, wherein the at least one processor is further configured to visualize the detailed analysis information together with a menu configured to allow a user to input feedback on the user's approval for or rejection of at least one of the intermediate result of the first process and the final result of the second process.

4. The medical image visualization apparatus of claim 3, wherein the at least one processor is further configured to, when the user approves at least one of the intermediate result and the final result, store an indication of the user's approval of at least one of the intermediate result and the final result in association with the at least one medical image and the detailed analysis result in a database.

5. The medical image visualization apparatus of claim 1, wherein the at least one processor is further configured to:
   connect a work environment menu configured to allow a user to manually modify at least one of the intermediate result and the final result with the connection image; and
   provide the work environment menu together with the detailed analysis information.

6. The medical image visualization apparatus of claim 1, wherein the detailed analysis information includes:
   a preprocessing result of the original medical image as the intermediate result; and
   a quantitative analysis result of the original medical image, generated based on the preprocessing result, as the final result.

7. The medical image visualization apparatus of claim 1, wherein the detailed analysis information includes:
   an object identification result of the original medical image as the intermediate result; and
   a filtering result, obtained by applying a threshold to the object identification result, as the final result.

8. The medical image visualization apparatus of claim 1, wherein the at least one processor is further configured to:
   connect a menu configured to allow a user to edit the at least one medical image or to generate a new medical image in which settings of the at least one medical image are adjusted with the connection image; and
   provide the menu together with the detailed analysis information.

9. The medical image visualization apparatus of claim 8, wherein the at least one processor is further configured to:
   connect a work environment menu configured to, when the at least one medical image is at least one of an reconstructed image and a reformatted image of the original medical image, allow the user to generate at least one of a new reconstructed image and a new reformatted image as a new medical image by adjusting at least one of a range, an angle, a viewpoint, and an option in, at, from, and in which the at least one of the reconstructed image and the reformatted image is generated with the connection image; and
   provide the work environment menu together with the detailed analysis information.

10. The medical image visualization apparatus of claim 8, wherein the at least one processor is further configured to:
    connect a work environment menu configured to, when the at least one medical image includes a report indicative of the image analysis result, allow the user to generate a new report by adjusting at least one parameter used to generate the report with the connection image; and
    provide the work environment menu together with the detailed analysis information.

11. The medical image visualization apparatus of claim 8, wherein the at least one processor is further configured to:
    connect a work environment menu configured to, when the detailed analysis information includes an object identification result of the original medical image, allow the user to correct a threshold applied to the object identification result, to generate a result obtained by performing filtering while applying a modified threshold as new detailed analysis information, or to manually verify the object identification result before a threshold is applied with the connection image; and
    provide the work environment menu together with the detailed analysis information.

12. A medical image visualization method comprising:
    acquiring or receiving, by at least one processor, at least one medical image by controlling a reception interface;
    recognizing, by the at least one processor, a connection image that is presented on the at least one medical image and connects the at least one medical image and detailed analysis information regarding the at least one medical image;

acquiring, by the at least one processor, the detailed analysis information, connected to the at least one medical image by the connection image; and visualizing, by the at least one processor, the detailed analysis information on a display, wherein the detailed analysis information includes an intermediate result of a first process, in which the intermediate result is generated based on an original medical image, and a final result of a second process, in which the final result is generated at least based on the intermediate result, and the at least one medical image is generated by imaging the final result, wherein the at least one medical image includes the final result including at least one of a finding result, a diagnosis result, a threshold-based filtering result, or a quantified analysis result related to at least one region or object, and wherein the intermediate result includes at least one of a segmentation result or an identification result of the at least one region or object, as a preprocessing result of the final result.

\* \* \* \* \*